(12) United States Patent
Khawand

(10) Patent No.: US 11,490,338 B1
(45) Date of Patent: Nov. 1, 2022

(54) MOTION-RESPONSIVE TRANSMISSION POWER MANAGEMENT

(71) Applicant: Microsoft Technology Licensing, LLC, Redmond, WA (US)

(72) Inventor: Charbel Khawand, Sammamish, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 17/329,757

(22) Filed: May 25, 2021

(51) Int. Cl.
*H04B 17/318* (2015.01)
*H04W 52/28* (2009.01)
*H04W 4/029* (2018.01)

(52) U.S. Cl.
CPC ........ *H04W 52/285* (2013.01); *H04B 17/318* (2015.01); *H04W 4/029* (2018.02)

(58) Field of Classification Search
CPC ... H04W 52/285; H04W 4/029; H04B 17/318
USPC ........................................................ 455/522
See application file for complete search history.

(56) References Cited

U.S. PATENT DOCUMENTS

| | | | | |
|---|---|---|---|---|
| 4,723,124 | A * | 2/1988 | Boles | G01S 13/9023 342/25 C |
| 7,394,451 | B1 | 7/2008 | Patten et al. | |
| 8,154,435 | B2 * | 4/2012 | Pett | G01S 13/867 342/25 R |
| 8,515,496 | B2 * | 8/2013 | Cheng | H01Q 1/243 343/702 |
| 8,886,980 | B2 | 11/2014 | Kulik | |
| 8,989,792 | B1 | 3/2015 | Depew | |
| 9,331,730 | B2 | 5/2016 | Zhang et al. | |
| 9,468,492 | B2 * | 10/2016 | Podhajsky | A61B 18/1477 |

(Continued)

FOREIGN PATENT DOCUMENTS

| | | |
|---|---|---|
| AU | 2015202940 A1 | 6/2015 |
| CN | 106034351 A * | 10/2016 |
| WO | 2012143936 A1 | 10/2012 |

OTHER PUBLICATIONS

Semtech Launches Smart Proximity Sensor for Short-Range Human Presence Detection & SAR Regulations in Mobile & Tablet PC Applications, Retrieved from https://investors.semtech.com/news-releases/news-release-details/semtech-launches-smart-proximity-sensor-short-range-human, Jul. 24, 2012, 2 Pages.

(Continued)

*Primary Examiner* — Hai V Nguyen
(74) *Attorney, Agent, or Firm* — Holzer Patel Drennan

(57) ABSTRACT

Transmission power of a communication device is managed by detecting motion of the communication device using a motion sensor, classifying detected motion according to one or more motion classification conditions using one or more motion classification parameters, adjusting the one or more motion classification parameters applied to the classifying operation, responsive to the classifying operation, classifying the detected motion according to the one or more motion classification conditions using the one or more adjusted motion classification parameters, and adjusting the transmission power of the communication device based at least in part on the one or more motion classification conditions and the one or more adjusted motion classification parameters, responsive to the operation of classifying using the one or more adjusted motion classification parameters.

20 Claims, 9 Drawing Sheets

(56) References Cited

U.S. PATENT DOCUMENTS

| | | | |
|---|---|---|---|
| 9,494,675 B2* | 11/2016 | McCorkle | G01S 13/106 |
| 9,531,420 B1 | 12/2016 | Prendergast et al. | |
| 9,628,124 B1* | 4/2017 | Srivastava | H04W 4/70 |
| 9,813,997 B2 | 11/2017 | Mercer et al. | |
| 9,871,545 B2* | 1/2018 | Khawand | H04B 1/3838 |
| 10,013,038 B2 | 7/2018 | Mercer et al. | |
| 10,180,362 B2* | 1/2019 | Alon | G01K 11/006 |
| 10,204,504 B1* | 2/2019 | Lin | G01P 15/18 |
| 10,251,701 B2* | 4/2019 | Willyard | A61B 18/1815 |
| 10,382,614 B2* | 8/2019 | Novet | H04M 1/72454 |
| 10,514,769 B2* | 12/2019 | Aurongzeb | G06F 3/017 |
| 10,588,684 B2* | 3/2020 | Podhajsky | A61B 18/1206 |
| 10,686,538 B2 | 6/2020 | Seyed et al. | |
| 11,058,488 B2* | 7/2021 | Brannan | A61B 18/1815 |
| 11,073,584 B2* | 7/2021 | Takeshima | G01R 33/4824 |
| 11,147,622 B2* | 10/2021 | Willyard | A61B 18/1815 |
| 11,228,810 B1* | 1/2022 | Arazi | H04N 21/251 |
| 11,231,437 B1* | 1/2022 | Alnajjar | A61B 5/1123 |
| 2010/0045513 A1* | 2/2010 | Pett | G01S 13/867 |
| | | | 342/25 C |
| 2012/0142291 A1* | 6/2012 | Rath | H04B 7/0613 |
| | | | 455/127.1 |
| 2013/0156080 A1* | 6/2013 | Cheng | H04M 1/72454 |
| | | | 375/267 |
| 2014/0213192 A1* | 7/2014 | Lagnado | H04W 52/0254 |
| | | | 455/67.11 |
| 2014/0313071 A1* | 10/2014 | McCorkle | G01S 13/106 |
| | | | 342/202 |
| 2016/0164563 A1* | 6/2016 | Khawand | H04W 52/221 |
| | | | 455/127.2 |
| 2016/0352784 A1* | 12/2016 | Oh | H04W 4/02 |
| 2017/0200032 A1* | 7/2017 | Sample | G06K 7/10396 |
| 2018/0107341 A1* | 4/2018 | Aurongzeb | G06F 3/017 |
| 2018/0224871 A1* | 8/2018 | Sahu | G06F 1/3231 |
| 2018/0259341 A1* | 9/2018 | Aboutalib | B64C 39/024 |
| 2019/0070064 A1* | 3/2019 | Hogle | G16H 40/63 |
| 2019/0387168 A1* | 12/2019 | Smith | H04N 5/23245 |
| 2020/0029863 A1* | 1/2020 | Kiourti | A61B 5/6804 |
| 2020/0088824 A1* | 3/2020 | Takeshima | G01R 33/5673 |
| 2020/0174115 A1* | 6/2020 | Prados | G01S 13/90 |
| 2020/0195290 A1* | 6/2020 | Khawand | H04W 52/226 |
| 2020/0205087 A1 | 6/2020 | Hong | |
| 2021/0051465 A1* | 2/2021 | Koshy | H04W 24/10 |
| 2021/0188541 A1* | 6/2021 | Kurani | B65F 1/14 |
| 2021/0263309 A1* | 8/2021 | Rivera Cintron | G06F 1/3265 |

OTHER PUBLICATIONS

Riaan, Du Toit, "Using proximity sensing to meet mobile device FCC SAR regulations", Retrieved from: https://www.azoteq.com/wp-content/uploads/2018/11/Azoteq_Newsletter-May 2012.pdf, May 2012, 6 Pages.

Pell, Rich, "Smart Sensor Controls Human Body RF Exposure", Retrieved from: https://www.eenewseurope.com/news/smart-sensor-controls-human-body-rf-exposure. Aug. 2, 2017, 2 pages.

"International Search Report & Written Opinion issued in PCT Application No. PCT/US22/026856", dated Aug. 23, 2022, 10 Pages.

* cited by examiner

MOTION-RESPONSIVE TRANSMISSION POWER MANAGEMENT

BACKGROUND

Communication devices emit electromagnetic radio frequency signals to transmit and receive data. Safety concerns about absorbed radiation from the radio frequency signals transmitted have led regulatory bodies, such as the Federal Communications Commission, to set Specific Absorption Rate (SAR) regulations limiting the amount of radiation absorbed by a user of a communication device. Compliance with SAR regulations often involves reducing the transmission power of communication antennas in the communication device, which generally reduces transmission performance.

SUMMARY

The described technology provides implementations of systems and methods for power management in a communication device. More specifically, the described technology provides implementations of systems and methods for SAR-related power management in a communication device.

For example, a method of managing transmission power of a communication device is provided. The method includes detecting motion of the communication device using a motion sensor, classifying detected motion according to one or more motion classification conditions using one or more motion classification parameters, adjusting the one or more motion classification parameters applied to the classifying operation, responsive to the classifying operation, classifying the detected motion according to the one or more motion classification conditions using the one or more adjusted motion classification parameters, and adjusting the transmission power of the communication device based at least in part on the one or more motion classification conditions and the one or more adjusted motion classification parameters, responsive to the operation of classifying using the one or more adjusted motion classification parameters.

This summary is provided to introduce a selection of concepts in a simplified form that is further described below in the Detailed Description. This summary is not intended to identify key features or essential features of the claimed subject matter, nor is it intended to be used to limit the scope of the claimed subject matter.

Other implementations are also described and recited herein.

BRIEF DESCRIPTIONS OF THE DRAWINGS

DETAILED DESCRIPTIONS

Figure 1:
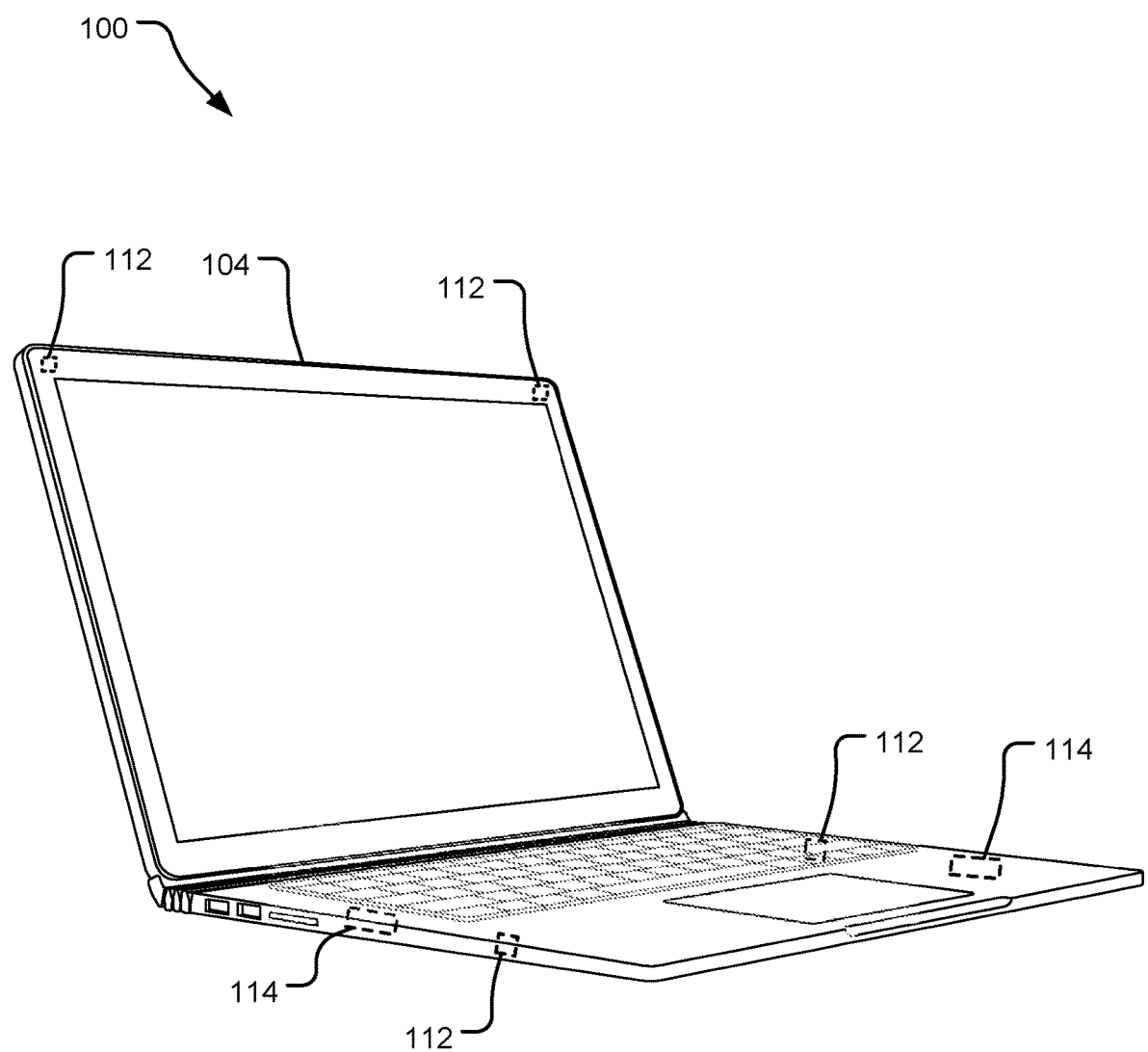
FIG. 1 illustrates an example communication device system.

Consumer electronic devices may be equipped with wireless communication circuitry emitting radio frequency (RF) electromagnetic fields that can be absorbed by human tissue positioned in close proximity to the wireless communication circuitry. For example, the wireless communications circuitry may transmit and receive RF signals in mobile telephone RF bands, LTE RF bands, Wi-Fi network RF bands, and GPS RF bands. To protect humans from harmful levels of RF radiation when using such devices, government agencies have imposed regulations limiting RF transmission power from some wireless electronic devices, such as tablet computers and mobile phones.

In some jurisdictions, specific absorption rate (SAR) standards set maximum time-averaged energy absorption limits on electronic device manufacturers. These standards impose restrictions on the time-averaged amount of electromagnetic radiation that may be emitted during a rolling time window within a given distance of a transmitting radio frequency (RF) antenna. Particular attention is given to radiation limits at distances within a few centimeters from the device (e.g., 0-3 centimeters), where users are likely to place a human body part near the transmitting antenna. For example, the U.S. Federal Communications Commission (FCC) imposes a regulation under which phones sold in the United States have an average SAR level at or below 1.6 watts per kilogram (W/kg) taken over the volume containing a mass of 1 gram of tissue that is absorbing the most signal. Different regulations may be imposed for different types of devices (e.g., phone, tablet computer) and for different body parts (e.g., torso, hands, legs) in the proximity of an RF transmitting antenna. Such restrictions may be satisfied by reducing the transmitted RF signal strength when a dielectric body (e.g., a human body part) is detected in the proximity of the transmitting antenna. Such proximity detection can be performed in a variety of ways, such as capacitive sensing or other means of measuring signal interference.

While reducing transmitted RF signal strength may enhance user safety and/or compliance with local safety regulations, significant reductions in the transmitted carrier signal strength can result in decreased device communication performance, including without limitation dropped connections (e.g., a dropped call) and/or delays in the transmission of information. Furthermore, proximity detection typically involves a sensor that occupies scarce space within a communication device.

Detected motion of a communication device can indicate that a user is interacting with the communication device. However, a considerable amount of device motion can be attributable to other sources of motion, for example, motion of one or more of internal communication device componentry, of a surface on which a communication device rests (e.g., in a moving vehicle), attributable to an environment in which the communication device is located. Discriminating between motion that is likely attributable to human interaction with the communication device and other communication device motion can better inform when a SAR power backoff is appropriate, minimizing the time performance of the communication device is unnecessarily affected.

Discriminating between background motion and human interaction motion can be difficult, as there may be similarities between the two. One method for distinguishing between user-related motion, which should appropriately trigger a SAR motion backoff (hereinafter, "SAR IN MOTION state"), and background motion, which should indicate the motion is attributable to inanimate objects and not trigger SAR motion backoff (hereinafter, "SAR STATIONARY state"), is to tune a motion sensor to better distinguish between SAR motion states. SAR motion states may include a SAR IN MOTION state, a state in which detected motion indicates a user engages the communication device, and a SAR STATIONARY state, a state in which detected motion indicates a user is not engaged with the communication device. Depending on the detected motion and/or magnitude thereof, the motion may be tuned by classification parameters and classified according to a classification condition as being in or changing to a SAR motion state.

Classification parameters are tunable parameters of the motion detection elements in a communication device that are tuned to better emphasize motion attributable to human interaction relative to other background motion. For example, any number of classification parameters for processing detected motion signals may be adjusted responsively to a detected motion depending on whether the detected motion satisfies one or more motion classification conditions, especially in light of the existing classification parameters. Tunable classification parameters may include one or more of a sensitivity to detected motion, a sampling frequency of the detected motion, a variable window of sampling over which samples of detected motions may be assessed, frequency discrimination (e.g., between frequencies representing a SAR IN MOTION state and frequencies representing a SAR STATIONARY state), a magnitude of the detected motion (perhaps overall average magnitude or magnitude in certain frequencies), conditions used to ascertain whether the detected motion corresponds to a predetermined motion profile, and the motion profiles characterizing likely user interaction based on the detection motion and the like.

Classification conditions are used to classify the detected motion signal as being in a SAR motion state. Classification conditions may be used to determine whether the tunable classification parameters are adjusted, perhaps based on the detected SAR motion state and/or a predefined motion profile. Classification conditions may include without limitation comparisons, for example, between detected motions and one or more of thresholds or motion profiles. For example, the communication device may use the classification conditions to determine whether the detected motion is characteristic of a particular anticipated and/or predefined type of motion and/or represents either SAR IN MOTION or SAR STATIONARY states. The classification conditions may also be dynamic, perhaps responsive to adjustments made to the classification parameters and/or hysteresis with respect to prior SAR motion states.

The motion profiles may include any number of scenarios of use or nonuse anticipated with respect to the communication device, for example, one or more of the communication device resting on an inanimate surface with no user interaction (or with user interaction), resting on an inanimate surface in a moving vehicle with no user interaction (or with user interaction), resting on a lap but with no other user interaction with the device (e.g., no typing or scrolling), and active user interaction with the device. The scenario where the communication device rests on a user's lap but is otherwise not actively engaged by the user can present a particularly difficult scenario in which SAR IN MOTION activity should be flagged but could be confused with background motion and flagged as SAR STATIONARY. Another scenario is one in which the device rests on a table surface, and one must discern between a user being engaged and not engaged. A further scenario is one in which the user is holding the communication device but not otherwise moving. Tunable classification parameters may provide better resolution to emphasize the distinctions between likely user interactions and, consequently, between SAR motion states.

The motion sensor may be only one of a number of motion sensors in the communication device. The motion sensors may be situated or coupled in different parts of the communication device, tracking the motion of each of the different parts of the device. The locations may correspond to or be relevant to one or more transceiver components that emit electromagnetic radiation. This may be relevant, as the motion of different parts of the device individually and/or collectively can be indicative of different motion profiles. In implementations, the output of each of the motion sensors can be individually compared with motion profiles assessed within each motion sensor and/or can be output collectively to determine a motion profile and/or classify detected motion to determine a SAR motion state, perhaps using inferential software, such as machine learning, or applying predefined standards stored in software.

Any number of feedback mechanisms may be deployed wherein any of one or more outputs of one or more of motion sensors, a location of one or more motion sensors, classification parameters of one or more motion sensors, classification conditions of one or more motion sensors, a machine learning algorithm affecting motion any of the afore listed items, or predefined controlling software (e.g., in tables), without limitation, may interact and affect one another in dynamic and/or static manners.

FIG. 1 illustrates an example communication device system 100. The communication device 104 is any device capable of communicating wirelessly using electromagnetic radiation, for example, radio frequencies. The communication device 104 illustrated in FIG. 1 is a laptop, but it should be appreciated that any communication device that uses electronic communication is contemplated, for example, a mobile phone, desktop computer, server, tablet, hybrid 2-in-1 system. The communication device 104 may have one or more electronic transmitters 112. The one or more electronic transmitters 112 are elements that transmit electronic communications. The electronic transmitters 112 may include one or more of antennas, transceivers, and other communications components and may be configured to transmit in one or more electromagnetic frequency bands. The transmission power for the one or more electronic transmitters 112 can be limited in order to comply with regulatory standards for SAR compliance when a user interacts directly with the communication device 104. The transmission power supplied to or provided by the electronic transmitters 112 can be increased when a user does not interact directly with the communication device 104. The SAR requirements may be based at least in part on the locations of the one or more electronic transmitters 112 and the likelihood that a profile of user interaction involves user proximity to or engagement with the communication device 104.

In the illustrated implementation, the communication device 104 includes one or more motion sensors 114. The one or more motion sensors 114 are elements that detect motion of the communication device 104. It should be appreciated that the one or more motion sensors 114 may be implemented in software, dedicated hardware, or any combination thereof. In implementations, a motion sensor 114 detects the motion of the communication device 104 in a location at which the motion sensor 114 is located on or in the communication device 104. The motion sensor 114 can therefore be used to discern between SAR motion states in the communication device 104.

In the illustrated implementation, the motion sensor 114 includes a motion detector. The motion detector is an element that detects motion. The motion detector may be any element that detects motion, for example, a sensor that detects acceleration or changes in physical motion (e.g., a gyro, an accelerometer, etc.), a sensor that detects reflections of electromagnetic radiation (e.g., LIDAR, RADAR, etc.), or a sensor that detects reflections of sound (e.g., SONAR). In implementations where the motion detector is a sensor that detects acceleration or changes in physical motion, the sensor may be selected to satisfy an acceptable sensitivity minimum, for example, +/−125 degrees per second per least significant bit. For the purposes of this specification, a detected motion can be, for example, one or more of a single sample of detected motion, a motion representing a number of consecutive samples, a pattern of motion within a set of samples or time frame. The motion may be a pattern of motion indicative of a SAR motion state.

The motion sensor 114 may be positioned or coupled in the communication device 104 such that the motion detector is shielded from or distant from the motion of internal componentry of the communication device 104. For example, the motion detector may need to be shielded from or otherwise compensate for fan motion, speaker motion, drive motion, actuator motion, or any other internal motion of the device. Some of this background motion may be removed from the signal using a signal discriminator or may be computationally ignored based on existing predefined tables. These artifacts may also be removed or compensated for using motion profiles stored in the controller of the motion sensor 114 and/or other elements of the communication device 104. The motion detector may also be installed proximal to one or more electronic transmitters 112, such that any motion detected by the motion detector is indicative of the motion of the electronic transmitters 112 to which the motion detector is proximate.

The motion sensor 114 may have signal processing elements, for example, one or more of a sampler, a frequency renderer, a signal discriminator, and a smoother. The sampler samples detected motion to produce a discrete detected motion signal. The sampler may have a sample rate which may be a tunable classification parameter. An example of a sample rate is 100 Hz, and an example of a range of sample rates is greater than 100 Hz. The sample rate may be adjusted in some circumstances, for example, when a SAR motion state is changed from a prior SAR motion state. In an implementation, a detected motion may be classified using as a classification condition of a SAR IN MOTION state. The sampler may increase the sampling rate in order to better focus on the detected motion, perhaps to allow for precise detection of when a user is no longer engaged with the communication device 104 and allow for a quicker transition to a SAR STATIONARY state. AN increase in sampling may also be triggered if the device remains in SAR STATIONARY state for a long period of time. The sample rate may be decreased in some circumstances, for example, when a sufficient period (perhaps a decay interval) has passed in which the detected motion no longer indicates that a user is engaged with the communication device 104 such that the classification transitions from a SAR IN MOTION state to a SAR STATIONARY state. In implementations, when returning to a SAR STATIONARY state from a SAR IN MOTION state, the sampling rate may be returned to an originally provisioned level. Varying the sample rate may allow for better focus on samples in order to more quickly escape a SAR IN MOTION state, perhaps allowing for better performance.

The frequency renderer renders sampled motions detected into a frequency domain signal from a time/sample domain signal. Implementations exist where rendering the signal in a frequency domain representation is unnecessary, for example, when the motion sensor can operate on frequency domain elements using the time/sample domain signal. Operating on frequency elements may allow for better discernment between different signal elements that are attributable to human interaction and background motion.

The signal discriminator is an element that removes particular frequencies or frequency ranges from a signal representing the detected motion. The frequencies or frequency ranges removed may be a tunable classification parameter. The signal discriminator may be, for example, one or more of a high pass filter, low pass filter, bandpass filter, or digital software filter. The signal discriminator may be tunable to exclude frequencies likely indicative of background motion and include frequencies indicative of motion representing likely user interaction with the communication device 104. Examples of frequency ranges to be rolled off may include frequencies higher than one of 2 Hertz (Hz), 5 Hz, 10 Hz, 30 Hz, and 45 Hz. The signal discriminator may change the rolled-off frequencies dynamically. For instance, if a sufficient level of detected motion to classify detected motion as indicating a SAR IN MOTION state, the frequency ranges may be adjusted to better focus on the frequencies that represent user interaction with the communication device 104. If the detected motion in these frequencies is sufficiently low, the classification condition of the detected motion may be reclassified as indicating a SAR STATIONARY state, perhaps allowing an expansion of the frequencies accounted for in the signal. Distinguishing between frequencies that are attributable to human interaction may allow a better and simpler comparison for whether a threshold is meaningfully met for magnitudes of motion in the relevant frequencies.

The smoother is an element that smooths the signal. The smoother may help to reduce the effect of outliers and/or noise in the signal representing the detected motion. The smoother may render the signal into an energy representation. The smoother may use a mean square or root mean square average for smoothing the energy representation of consecutive or otherwise related samples. For example, the motion detector may demonstrate detected motion in more than one axis (e.g., x, y, and z axes from a particular reference). A direction-independent magnitude of the energy in the signals for each sample can be determined by taking the square of the signal representing detected in each coordinate and summing them. This can be seen in equation 1:

$$R(n)=x^2(n)+y_2(n)+z^2(n) \qquad (1)$$

In Equation 1, n represents a particular sample of detected motion, with x(n) being a signal representing detected motion in an x-direction, y(n) being a signal representing detected motion in a y-direction, and z(n) being a signal representing detected motion in a z-direction. The x(n), y(n), and z(n) directional signals are squared and summed to yield R(n), a sum of squares representing a direction-independent magnitude of energy in the signals.

The smoother may use a mean-squared function or a root-mean-squared function to smooth the direction-independent magnitude of energy in the signal. An example of a mean squared representation is shown in equation (2).

$$\text{Mean Squared} = \frac{1}{K+1} * \sum_{-K/2}^{K/2} |R(n)| \quad (2)$$

An example of a root-mean-squared representation is shown in equation (3).

$$\text{Mean Squared} = \sqrt{\frac{1}{K+1} * \sum_{-K/2}^{K/2} |R(n)|} \quad (3)$$

In equations 2 and 3, R(n) may be the aforementioned direction-independent magnitude of the energy in the signals, n may again refer to an independent sample, and K may be a variable window over which the samples are smoothed. For example, K=12 would imply that there are 12 samples.

The number of samples in the variable window may be a tunable classification parameter to adjust the sensitivity to the detected motion. Examples of numbers and ranges of numbers of samples in a variable window include 20 samples, 200 samples, at least 20 samples, at least 200 samples, and between 20 and 200 samples. The variable window may be narrowed to include fewer samples when, for example, a classifier of the controller classifies a detected motion as indicative of a SAR IN MOTION STATE. This narrowing of the field may give more resolution to the signal. The variable window may be expanded to include more samples or a smaller time frame when, for example, a classifier of the controller classifies a detected motion as indicative of a SAR STATIONARY state.

The smoother may otherwise tune sensitivity to detected motion using a sensitivity tuner. The sensitivity tuner is an element that varies sensitivity of the motion sensor 114 to a detected motion to particular samples of or frequency elements in the detected motion. In an implementation, the sensitivity may be modified by giving different weight to elements of the signal, for example, different weight to certain frequencies in the signal representing the detected motion, to certain samples (e.g., more recent samples) in the signal representing the detected motion, or other elements of the signal representing the detected motion. For example, the sensitivity tuner may increase sensitivity to detected motion when the classifier of the controller classifies a detected motion as indicative of a SAR IN MOTION state. The sensitivity may be lowered responsive to the classifier of the controller classifying the detected motion as indicative of a SAR STATIONARY state. Increasing sensitivity may allow the device to more quickly determine that the device can be brought to a SAR STATIONARY state with better transmission performance.

The motion sensor 114 may include a controller. The controller may be used, for example, to classify one or more periods of detected motion according to classification conditions, determine which classification parameters to adjust relative to the detected motion, determine to what particular type of motion profile the detected motion corresponds, determine the extent to which any power is adjusted, determine whether a classifier classifies according to a classification condition a detected motion as indicative of a SAR IN MOTION state or SAR STATIONARY state, or determine an output to transmit to the communication device 104 to allow the communication device 104 (e.g., its processor and memory and software systems) to determine a motion profile or SAR motion state, and what output to transmit to instruct a power adjuster to adjust power.

In an implementation, the controller may include a tunable classification parameter that is a threshold to which the output of a sensitivity tuner and/or the detected motion is compared. The threshold may be a magnitude threshold, for example, a magnitude of signal energy to which the signal representing the magnitude of the detected motion is compared. The magnitude of the energy to be compared to the threshold may be the mean squared or root mean squared output of the smoother or may include a sample-by-sample comparison. It should be appreciated that if a decision is made by the controller or another element of the communication device 104 to increase the sensitivity to motion of the motion sensor to better distinguish from background noise, the threshold may be dynamically changed to account for the increased sensitivity. The threshold may be an element of or responsive to a motion profile. The threshold may also be dynamic if certain signal elements are emphasized or omitted, perhaps based on a motion profile. For example, if the magnitude of more recent samples is increased for emphasis, the magnitude of the threshold may need to be correspondingly increased in order to account for the artificial increase in signal energy. The use of a dynamic threshold allows for more dynamic processing of different expected motion profiles and different expected use cases of the communication device 104. The communication device 104 may benefit from using appropriate thresholds for appropriate circumstances.

Another example may be that the threshold needs to be reduced when certain frequencies are omitted to account for the expected loss of energy in the excluded elements. A basis for comparison of whether detected motion represents SAR IN MOTION state user interaction motion or SAR STATIONARY state background motion may be a noise floor. A noise floor typically represents motion attributed to elements of the device itself and, perhaps, minor motion indicative of stationary or relatively stationary environments. In one implementation, a mean square representation, as shown above in equation 2 (or, alternatively, a root mean square as shown in equation 3), may be used in a stationary environment. This may set a baseline for expected background motion for interaction with inanimate elements. A threshold may be set relative to a determined noise floor associated with, for example, one or more of the type of device, a motion profile to applied, and a baseline or default noise floor.

In another implementation, the magnitude of individual frequency components may be compared, rather than an overall magnitude of the signal energy. For example, magnitudes of certain frequencies can be compared with respect to expected motion profiles to determine a most likely motion profile that corresponds to the distribution of magnitudes of energy of the signal at different frequencies. When a user interacts with the communication device 104, the motion detector may be able to detect motions specific to a human body, for example, one or more of cardiovascular heartbeat, pulse, other measures of blood flow, or other natural human motions. Detection of a process indicating user interaction, even if it is small in magnitude, may be sufficient to trigger a SAR IN MOTION state and compel the controller or other element of the communication device 104 to adjust transmission power to the transmitters in the communication device 104. In still another implementation, the sensitivity may be used to better determine a specific motion profile, such that any transmission power adjustments made are based on the motion profile. The motion sensor may adjust the one or more motion classification parameters based at least in part on the predefined motion profile.

The controller may itself classify a detected motion according to a classification condition (e.g., a SAR motion state) or may indicate as much to a monitoring service of the communication device 104 to classify the SAR motion state. For example, the monitoring service may take as input the outputs of more than one controller of the plurality of motion sensors 114 to classify a SAR motion state and, correspondingly, determine whether transmission power needs to be backed off or may be increased.

An implementation of classifying according to a classification condition may be comparing a Mean Ratio with a threshold value. A mean ratio may be calculated using equation 4:

$$\text{Mean Ratio} = \frac{\text{Mean(Human)}}{\text{Mean(Inanimate)}} \quad (4)$$

The Mean Ratio is represented in equation 4 as a Mean (Human), a mean of detected motion signal energy when a user interacts with the communication device 104, divided by a Mean(Inanimate), a mean of detected motion signal energy when a user does not interact with the communication device 104. The threshold value for the Mean Ratio may vary depending on circumstances, for example, one or more of a sensitivity to motion (where recent sample energies or other elements of the signal may receive greater weight relative to other elements), a motion profile representing the expected type of motion detected. Implementations of the Mean Ratio may include, for example, ratios of 1.2, 1.3, 1.4, 1.5, 1.6, 1.7, 1.8, 1.9, 2, 2.1, 2.2, 2.3, 2.4, 2.5, 2.6, or 2.7 or may be in ranges of Mean Ratios, for example ranges 1.2-2, 1.2-2.5, 1.8-2.2, 1.9-2.1. The threshold may be increased in order to accommodate artificial increases in the signal energy to increase sensitivity or to better account for particular motion profiles. The threshold may be decreased in order to accommodate artificial decreases in the signal energy (e.g., excluding signal energy of certain excluded signal elements) to decrease sensitivity or to better account for particular motion profiles. If the Mean Ratio exceeds the threshold (i.e., satisfies a classification condition to show SAR IN MOTION), the motion sensor 114 may determine the motion detected represents user interaction with the communication device 104. The motion sensor 114 may, on its own, one or more of trigger the SAR motion state and adjust the transmission power of the communication device 104. Alternatively or additionally, the motion sensor 114 may transmit the output of the Mean Ratio comparison to the threshold to an element of the communication device 104 to allow the communication device 104 to determine or classify, perhaps in concert with other outputs of other motion sensors 114, one or more of a SAR motion state, power transmission adjustment instructions, and a relevant or appropriate motion profile corresponding to a pattern of activity associated with the detected motion(s).

The controller may also maintain the SAR IN MOTION state for a period of time, perhaps a decay interval. A decay interval is a period of time or corresponding samples over which the SAR IN MOTION state remains triggered based on the detected motion continuing to indicate SAR IN MOTION. The decay interval may require a certain time frame or a number of samples over which the detected motion indicates no user interaction motion before a SAR IN MOTION state is no longer triggered. In an implementation, a decay interval may require 15 seconds or 15 samples where a classification condition (e.g., threshold) is not met, indicating the device is experiencing only background motion indicating a SAR STATIONARY state. The decay interval may be increased if the detected motion indicates there has been a longer or more pronounced pattern of user engagement with the communication device 104. The decay interval may be decreased if the detected motion indicates that there has been no or a short or less pronounced pattern of user engagement with the communication device 104. The decay interval over which a SAR motion state may be based at least in part on the detected motion is maintained. The ability to manipulate the decay interval may also allow for a more versatile SAR state control mechanism. If the communication device 104 identifies that the signal has sufficiently decayed or that the signal that triggered a SAR IN MOTION state is erroneous or fleeting, the decay interval can be reduced or otherwise modified to accommodate.

When a controller has classified according to a classification condition, the controller may responsively adjust one or more of the classification parameters based on whether the one or more classification conditions are satisfied. The controller may further responsively adjust the one or more classification conditions responsive to the satisfaction of the one or more classification conditions, based on one or more of the satisfaction of the one or more classification conditions and any adjustments made to the classification parameters.

For example, in an implementation, if the controller has determined over prior samples that motion sensor 114 (and/or communication device 104) is in a SAR STATIONARY state, a next detected motion sample may be sufficient (e.g., yield a signal of sufficient energy magnitude) to satisfy a classification condition (e.g., exceed a threshold), such that the device is determined to likely be in a SAR IN MOTION state. The controller may focus more on the motion by increasing the motion sensitivity, perhaps by means of a sensitivity tuner. The sensitivity may be changed by giving different weights to samples and/or frequency elements in the samples. The controller may alternatively or additionally correspondingly change the threshold to better focus the detection of the motion. The controller may alternatively or additionally modify the sample rate to get a more or less precise reading of the motion detected. The controller may alternatively or additionally expand or contract a variable window in order to adjust the smoothness of the representation of the signal magnitude for comparison. The controller may alternatively or additionally modify the decay interval, perhaps requiring more or fewer samples indicating a SAR STATIONARY state before transitioning from a SAR IN MOTION state to a SAR STATIONARY state.

In implementations, the motion sensor 114 may be in communication with a SAR manager, perhaps by means of a platform sensor application programming interface. Depending on the capabilities of the platform, the motion sensor 114 may be part of a default sensor stack, or a platform environment may provide an original equipment manufacturer the ability to create a custom sensor that can be accessed like a regular sensor via the platform sensor API.

In implementations, the motion sensor 114 may have elements that malfunction and/or fail to report results as expected. These may trigger a sensor failure state in the controller of the communication device 104. In a sensor failure state, the communication device may default to transmission power indicative of a SAR IN MOTION state to be safe. Implementations may further have a sensor sleep state. If no subscription is active, the controller or SAR manager may default to a SAR safety state while the SAR motion framework is in sleep states.

The controller or SAR manager may include or be in communication with a power adjuster responsible for adjusting the transmission power of the communication device 104. The power adjuster may adjust the power based at least in part on the one or more motion classification conditions and the one or more adjusted motion classification parameters, responsive to the operation of classifying using the one or more adjusted motion classification parameters. The transmission power may be reduced when the communication device 104 switches to a SAR IN MOTION state and may be increased when the communication device 104 switches to a SAR STATIONARY state.

Figure 2:
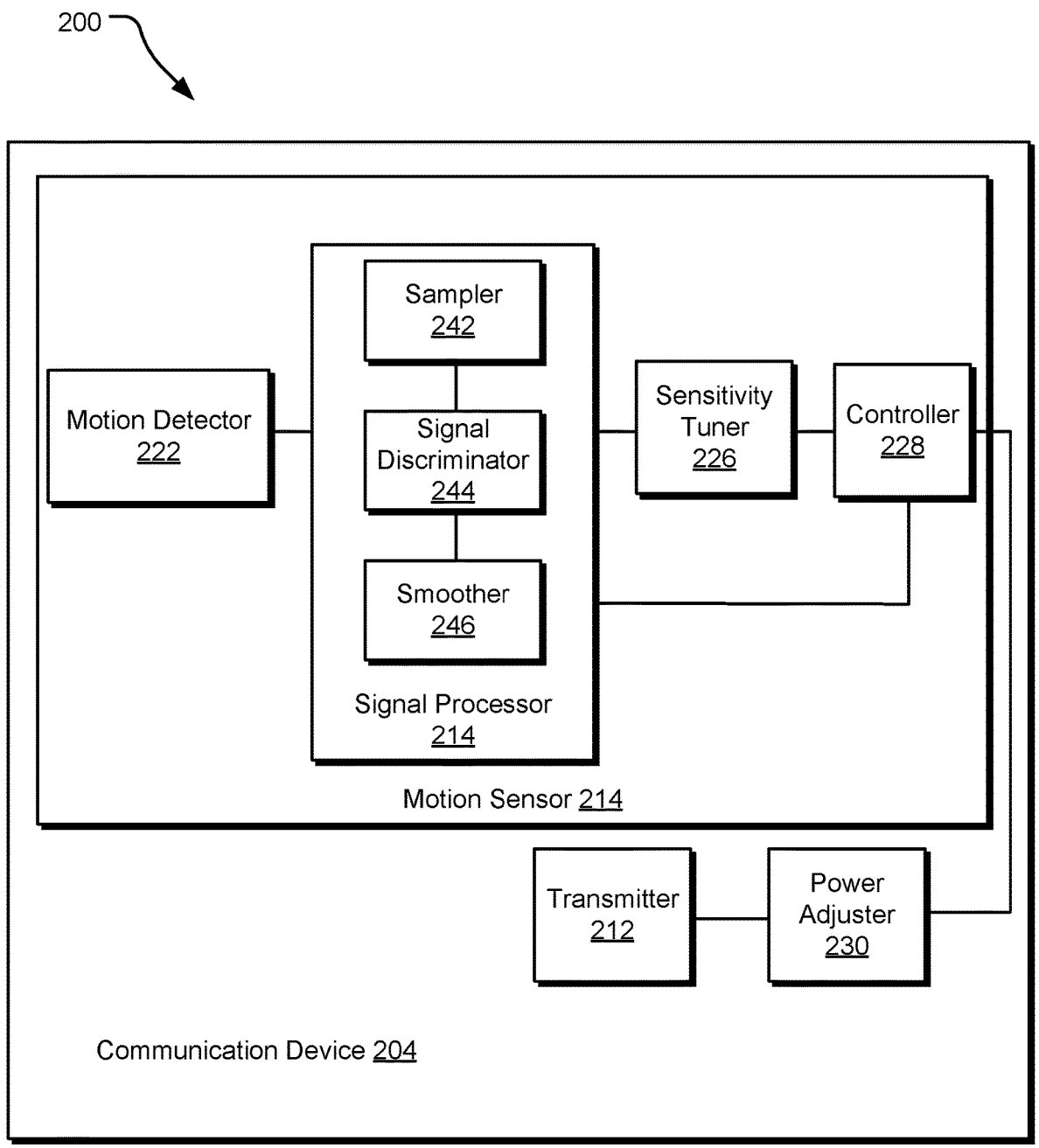
FIG. 2 illustrates another example communication device system.

FIG. 2 illustrates another example communication device system 200. The system 200 has a communication device 204 with a motion sensor 214, a power adjuster 230, and a transmitter 212. The communication device 204, the transmitter 212, and the motion sensor 214 may be implementations of the communication device 104, the transmitter 112, and the motion sensor 114, respectively. The motion sensor 214 may be positioned or coupled in the communication device 204 such that the motion detector 222 is shielded from or distant from the motion of internal componentry of the communication device. For example, the motion detector 222 may need to be shielded from or compensate for fan motion, speaker motion, drive motion, actuator motion, or any other known internal motion of the communication device 204. Some of this background motion may be excluded from the signal using a signal discriminator 244 or may be computationally ignored or removed based on predefined tables. These artifacts may also be removed or compensated for using motion profiles stored in a controller 228 of the motion sensor 214 and/or other elements of the communication device 204. The motion sensor 214 may also be installed proximal to one or more electronic transmitters, such that any motion detected by the motion detector 222 is indicative of the motion of the electronic transmitters to which the motion detector 222 is proximate.

The motion sensor 214 may have a signal processor 224 with signal processing elements, for example, one or more of a sampler 242, a frequency renderer (not shown), a signal discriminator 244, and a smoother 246. The sampler 242 is an element that samples detected motion to produce a discrete detected motion signal. The sampler 242 may have a sample rate which may be a tunable classification parameter. The sample rate may be increased in some circumstances, for example, when a SAR motion state is changed from a prior SAR motion state. In an implementation, a detected motion may be classified according to a classification condition as a SAR IN MOTION state. The sampler may increase the sampling rate in order to better focus on the detected motion, perhaps to allow for precise detection of when a user is no longer engaged with the communication device and allow for a quicker transition to a SAR STATIONARY state. The sample rate may be decreased in some circumstances, for example, when a sufficient period (perhaps a decay interval) has passed in which the detected motion no longer indicates that a user is engaged with the communication device 204 such that the classification condition transitions the SAR Motion state from a SAR IN MOTION state to a SAR STATIONARY state.

The frequency renderer (not shown) renders sampled motions detected into a frequency domain signal from a time/sample domain signal. Implementations exist where rendering the signal in a frequency domain representation is unnecessary, such that the motion sensor 214 can operate on frequency domain elements using the time-domain signal.

The signal discriminator 244 is an element that removes particular frequencies or frequency ranges from a signal representing the detected motion. The frequencies or frequency ranges removed may be a tunable classification parameter. The signal discriminator may be, for example, one or more of a high pass filter, low pass filter, bandpass filter, or digital software filter. The signal discriminator may be tunable to exclude frequencies predetermine to likely be indicative of background motion and include frequencies indicative of motion predetermined to likely representing user interaction with the communication device 104. The signal discriminator 244 may change the rolled-off frequencies dynamically. For instance, if a sufficient level of detected motion to classify detected motion as a SAR IN MOTION state, the frequency ranges may be adjusted to better focus on the frequencies that represent user interaction with the communication device 204. If the detected motion in these frequencies is sufficiently low, the detected motion may be reclassified according to a classification condition as SAR STATIONARY, perhaps allowing an expansion of the frequencies accounted for in the signal.

The smoother 246 is an element that smooths the signal. The smoother may help to reduce the effect of outliers and/or noise in the signal representing the detected motion. The smoother 246 may render the signal into an energy representation. The smoother may also use a mean square or root mean square average for smoothing energy representation of consecutive or otherwise related samples. More specifically, the motion detector 422 may demonstrate detected motion in more than one axis (e.g., x, y, and z axes from a particular reference). A direction-independent magnitude of the energy in the signals for each sample can be determined by taking the square of the signal representing motion detected in each coordinate and summing them. This can be seen in equation 1. The smoother 246 may use a mean-squared function or a root-mean-squared function to smooth the direction-independent magnitude of energy in the signal. An example of a mean squared representation is shown in equation (2). An example of a root-mean-squared representation is shown in equation (3).

The number of samples in the variable window may be a tunable classification parameter to adjust the sensitivity to the detected motion. Examples of numbers and ranges of numbers of samples in a variable window include, for example, 20 samples, 200 samples, at least 20 samples, at least 200 samples, between 20 and 200 samples. The variable window may be narrowed to include fewer samples when, for example, a classifier of the controller classifies a detected motion as indicative of a SAR IN MOTION STATE. This narrowing of the field may give more resolution to the signal. The variable window may be expanded to include more samples or a smaller time frame when, for example, a classifier of the controller classifies a detected motion as indicative of a SAR STATIONARY state.

The smoother 246 may otherwise tune sensitivity to detected motion using a sensitivity tuner 226. The sensitivity tuner 226 is an element that varies sensitivity of the motion sensor 214 to a detected motion to particular samples of or frequency elements in the detected motion. In an implementation, the sensitivity may be modified by giving different weight to elements of the signal, for example, different weight to certain frequencies in the signal representing the detected motion, to certain samples (e.g., more recent samples) in the signal representing the detected motion, or other elements of the signal representing the detected motion. For example, the sensitivity tuner 226 may increase sensitivity to detected motion when the classifier of the controller 228 classifies a detected motion as indicative of a SAR IN MOTION state. The sensitivity may be lowered responsive to the classifier of the controller classifying the detected motion as indicative of a SAR STATIONARY state.

The motion sensor 214 may include the controller 228, although the controller 228 may be implemented separately. The controller 228 may be used, for example, to classify one or more of detected motions according to classification conditions, determine which classification parameters to adjust relative to the detected motion, determine to what particular type of motion profile the detected motion corresponds, determine the extent to which any power is adjusted, determine whether a classifier classifies according to a classification condition a detected motion as indicative of a SAR IN MOTION state or SAR STATIONARY state, or determine an output to transmit to the communication device 204 to allow the communication device 204 (e.g., its processor and memory and software systems) to determine a motion profile or SAR motion state, and what output to transmit to instruct a power adjuster to adjust power.

In an implementation, the controller 228 may include a tunable classification parameter that is a threshold to which the output of a sensitivity tuner and/or the detected motion is compared. The threshold may be a magnitude threshold, for example, a magnitude of signal energy to which the signal representing the magnitude of the detected motion is compared. The magnitude of the energy to be compared to the threshold may be the mean squared or root mean squared output of the smoother or may include a sample-by-sample comparison. It should be appreciated that if a decision is made by the controller or another element of the communication device to increase the sensitivity to motion of the motion sensor 214 to better distinguish from background noise, the threshold may be dynamically changed to account for the increased sensitivity. The threshold may be an element of or responsive to a motion profile. The threshold may also be dynamic if certain signal elements are emphasized or omitted, perhaps based on a motion profile. For example, if the magnitude of more recent samples is increased for emphasis, the magnitude of the threshold may need to be correspondingly increased in order to account for the artificial increase in signal energy. Another example may be that the threshold needs to be reduced when certain frequencies are omitted to account for the expected loss of energy in the excluded elements.

A basis for comparison of whether detected motion represents SAR IN MOTION state user interaction motion or SAR STATIONARY state background motion may be a noise floor. A noise floor typically represents motion attributed to elements of the device itself and, perhaps, minor motion indicative of stationary or relatively stationary environments. In one implementation, a mean square representation, as shown above in equation 2 (or, alternatively, a root mean square as shown in equation 3), may be used in a stationary environment. This may set a baseline for expected background motion for interaction with inanimate elements. A threshold may be set relative to a determined noise floor for certain circumstances, for example, one or more of the type of communication device 204, a motion profile applied, and a baseline or default noise floor.

In another implementation, the magnitude of individual frequency components may be compared, rather than an overall magnitude of the signal energy. For example, magnitudes of certain frequencies can be compared with respect to expected motion profiles to determine a most likely motion profile that corresponds to the distribution of magnitudes of energy of the signal at different frequencies. When a user interacts with the communication device 204, the motion sensor 214 may be able to detect motions specific to a human body, for example, one or more of cardiovascular heartbeat, pulse, or other measures of blood flow.

Detection of a process indicating user interaction, even if it is of only a small magnitude, may be sufficient to trigger a SAR IN MOTION state and compel the controller 228 or another element of the communication device 204 to adjust transmission power (perhaps using a power adjuster 230) to the transmitters 212 in the communication device 204. In still another implementation, the sensitivity may be adjusted to better determine a specific motion profile, such that any transmission power adjustments made are based on a motion profile.

The controller 228 or SAR manager may include or be in communication with the power adjuster 230 responsible for adjusting the transmission power of the communication device 204. The power adjuster 230 may adjust the power based at least in part on one or more motion classification conditions and one or more adjusted motion classification parameters, responsive to the operation of classifying using the one or more adjusted motion classification parameters. The transmission power may be reduced when the communication device 204 switches to a SAR IN MOTION state and may be increased when the communication device 204 switches to a SAR STATIONARY state. The motion sensor 214 may adjust the one or more motion classification parameters based at least in part on a predefined motion profile The controller 228 may itself classify a detected motion according to a classification condition (e.g., a SAR motion state) or may indicate as much to a monitoring service of the communication device 204 to classify the SAR motion state. For example, the monitoring service may take as input the outputs of more than one controller 228 of the plurality of motion sensors 214 to classify a SAR motion state and, correspondingly, determine whether transmission power needs to be adjusted.

An implementation of classifying according to a classification condition may be comparing a Mean Ratio with a threshold value. A mean ratio may be calculated using equation 4. The threshold value for the Mean Ratio may vary depending on circumstances, for example, one or more of a sensitivity to motion (where recent sample energies or other elements of the signal may receive greater weight relative to other elements), a motion profile representing the expected type of motion detected. Implementations of the Mean Ratio may include, for example, ratios of 1.2, 1.3, 1.4, 1.5, 1.6, 1.7, 1.8, 1.9, 2, 2.1, 2.2, 2.3, 2.4, 2.5, 2.6, or 2.7 or may be in ranges of Mean Ratios, for example ranges 1.2-2, 1.2-2.5, 1.8-2.2, 1.9-2.1. The threshold may be increased in order to accommodate artificial increases in the signal energy to increase sensitivity or to better account for particular motion profiles. The threshold may be decreased in order to accommodate artificial decreases in the signal energy (e.g., excluding signal energy of certain excluded signal elements) to decrease sensitivity or to better account for particular motion profiles. If the Mean Ratio exceeds the threshold (i.e., satisfies a classification condition to show SAR IN MOTION), the motion sensor 214 may determine the motion detected represents user interaction with the communication device 204. The motion sensor 214 may, on its own, classify one or more of the detected motion according to a classification condition (e.g., SAR motion state) and adjust the transmission power of the communication device 204. Alternatively or additionally, the motion sensor 214 may transmit the output of the Mean Ratio comparison to the threshold to an element of the communication device 204 to allow the communication device 204 to determine or classify, perhaps in concert with other outputs of other motion sensors 214, one or more of a SAR motion state, power transmission adjustment instructions, and a relevant or appropriate motion profile corresponding to a pattern of activity associated with the detected motion(s).

The controller may also maintain the SAR IN MOTION state for a period of time, perhaps a decay interval. A decay interval is a period of time or corresponding samples over which the SAR IN MOTION state remains triggered based on the detected motion continuing to indicate SAR IN MOTION. The decay interval may require a certain time frame or a number of samples over which the detected motion indicates no user interaction motion before a SAR IN MOTION state is no longer triggered. In an implementation, a decay interval may require 15 seconds or 15 samples where a classification condition (e.g., threshold) is not met, indicating the device is experiencing only background motion of a SAR STATIONARY state. The decay interval may be dynamically responsive to any of, without limitation, the detected motion, a motion profile, a classification parameter, a classification condition, and a SAR state. The decay interval over which a SAR motion state is maintained may be based at least in part on the detected motion. The decay interval may be increased if the detected motion indicates there has been a longer or more pronounced pattern of user engagement with the communication device 204. The decay interval may be decreased if the detected motion indicates that there has been no or a short or less pronounced pattern of user engagement with the communication device 204.

When a controller 228 has classified detected motion according to a classification condition, the controller 228 may responsively adjust one or more of the classification parameters based on whether the one or more classification conditions are satisfied. The controller may further responsively adjust the one or more classification conditions responsive to the satisfaction of the one or more classification conditions, based on one or more of the satisfaction of the one or more classification conditions and any adjustments made to the classification parameters.

For example, in an implementation, if the controller 228 has determined over prior samples that motion sensor 214 (and/or communication device 204) is in a SAR STATIONARY state, a next detected motion sample may be sufficient (e.g., yield a signal of sufficient energy magnitude) to satisfy a classification condition (e.g., exceed a threshold), such that the device is determined to likely be in a SAR IN MOTION state. The controller 228 may focus more on the motion by increasing the motion sensitivity, perhaps by means of a sensitivity tuner. The sensitivity may be changed by giving different weights to samples and/or frequency elements in the samples. The controller 228 may alternatively or additionally correspondingly change the threshold to better focus the detection of the motion. The controller 228 may alternatively or additionally modify the sample rate to get a more or less precise reading of the motion detected. The controller 228 may alternatively or additionally expand or contract a variable window in order to adjust the smoothness of the representation of the signal magnitude for comparison. The controller 228 may alternatively or additionally modify the decay interval, perhaps requiring more or fewer samples indicating a SAR STATIONARY state before transitioning from a SAR IN MOTION state to a SAR STATIONARY state.

In implementations, the motion sensor 214 may be in communication with a SAR manager, perhaps by means of a platform sensor application programming interface. Depending on the capabilities of the platform, the motion sensor 214 may be part of a default sensor stack, or a platform environment may provide an original equipment manufacturer the ability to create a custom sensor that can be accessed like a regular sensor via the platform sensor API.

In implementations, the motion sensor 214 may have elements that malfunction and/or fail to report results as expected. These may trigger a sensor failure state in the controller of the communication device 204. In a sensor failure state, the communication device 204 may default to transmission power indicative of a SAR IN MOTION state to be safe. Implementations may further have a sensor sleep state. If no subscription is active, the controller 228 and/or SAR manager may default to a SAR safety state while the SAR motion framework is in sleep states.

Figure 3:
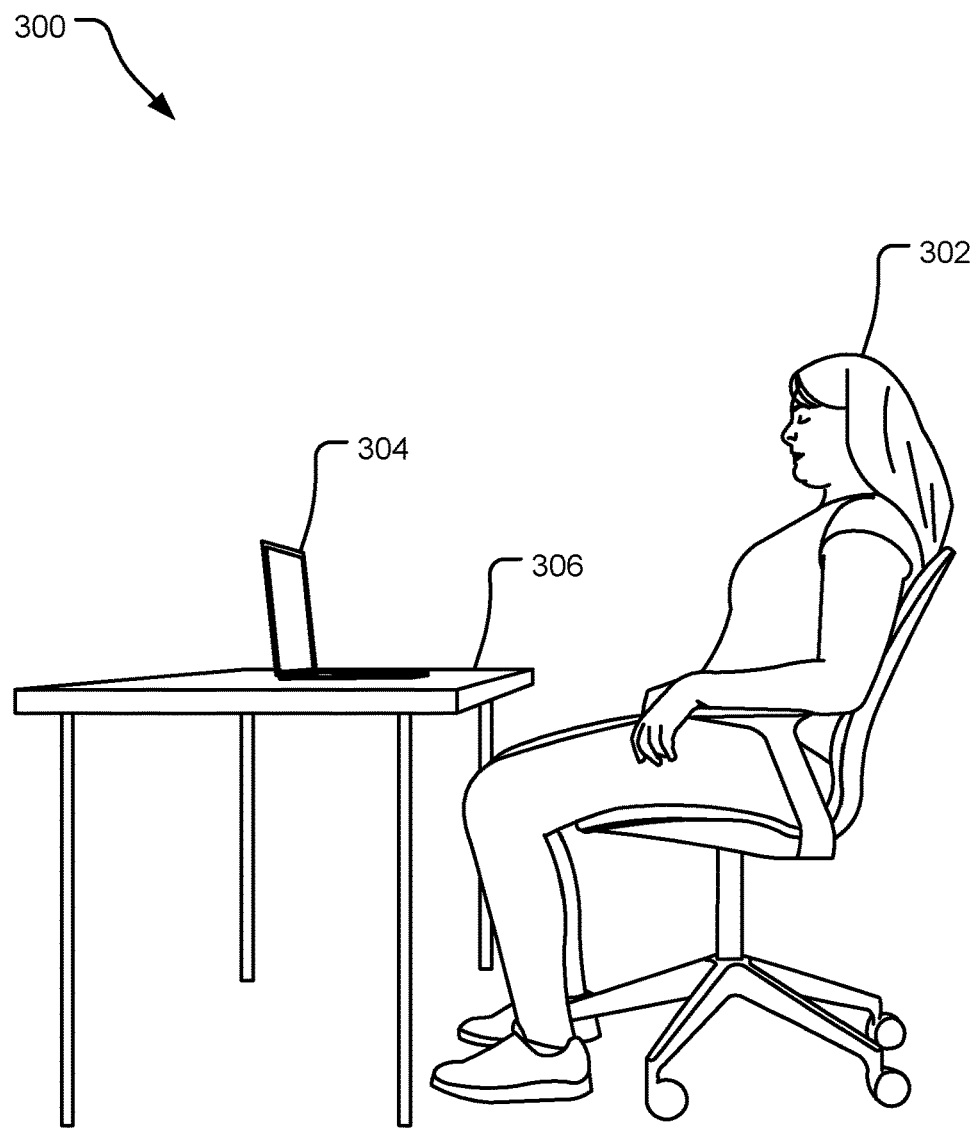
FIG. 3 illustrates an example use case of a motion sensor.

FIG. 3 illustrates an example use case 300 of the motion sensor. The use case 300 shows a communication device 304, an inanimate surface 306, and a seated user 302. The communication device 304 may be an implementation of communication device 104. The inanimate surface 306 is shown as a table on which the communication device 304 rests. In use case 300, the user is not engaged with the communication device 304. In this use case 300, the communication device 304 and its motion sensor do not detect motion indicative of user interaction with the communication device 304. As such, a classifier of a controller would classify the detected motion as a SAR STATIONARY state despite any background noise attributable to elements of the communication device 304 and the inanimate surface 306. Consequently, the SAR management system of the communication device 304 and/or a controller of the motion sensor may determine to increase or maintain maximum transmitter power in the communication device 304. If one or more of the classification parameters had been adjusted to accommodate a SAR IN MOTION state prior to the use case 300, the classification conditions and classification parameters may be readjusted to accommodate a SAR STATIONARY state. The use case 300 may also be classified as a communication device on an inanimate surface with no user engagement motion profile. Further, classification parameters may be adjusted accordingly.

Figure 4:
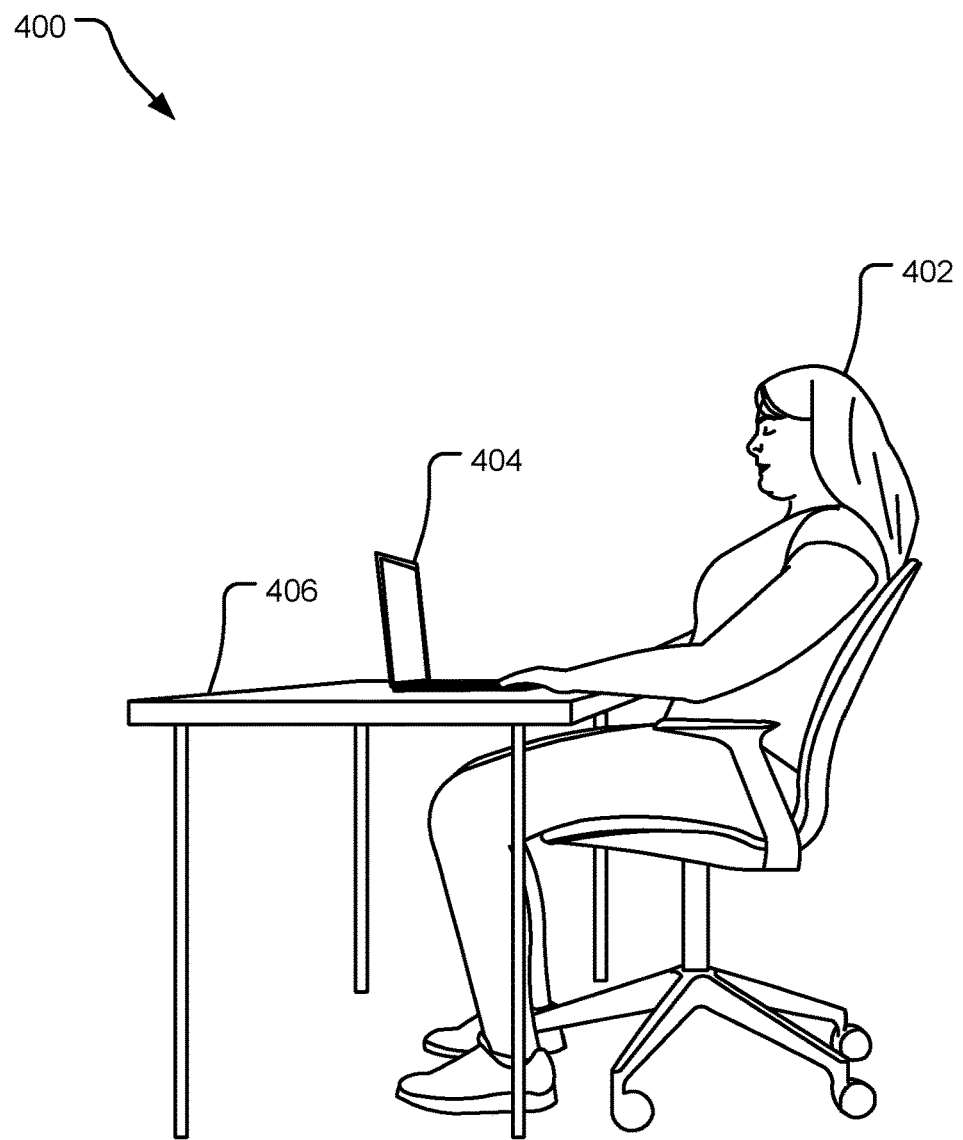
FIG. 4 illustrates another example use case of a motion sensor.

FIG. 4 illustrates another example use case 400 of the motion sensor. The use case 400 shows a communication device 404, an inanimate surface 406, and a seated user 402. The communication device 404 may be an implementation of communication device 104. The inanimate surface 406 is shown as a table on which the communication device 404 rests. In use case 400, the user is engaged with the communication device 404. In this use case 400, the communication device 404 and its motion sensor detect motion indicative of user interaction with the communication device 404.

Figure 5:
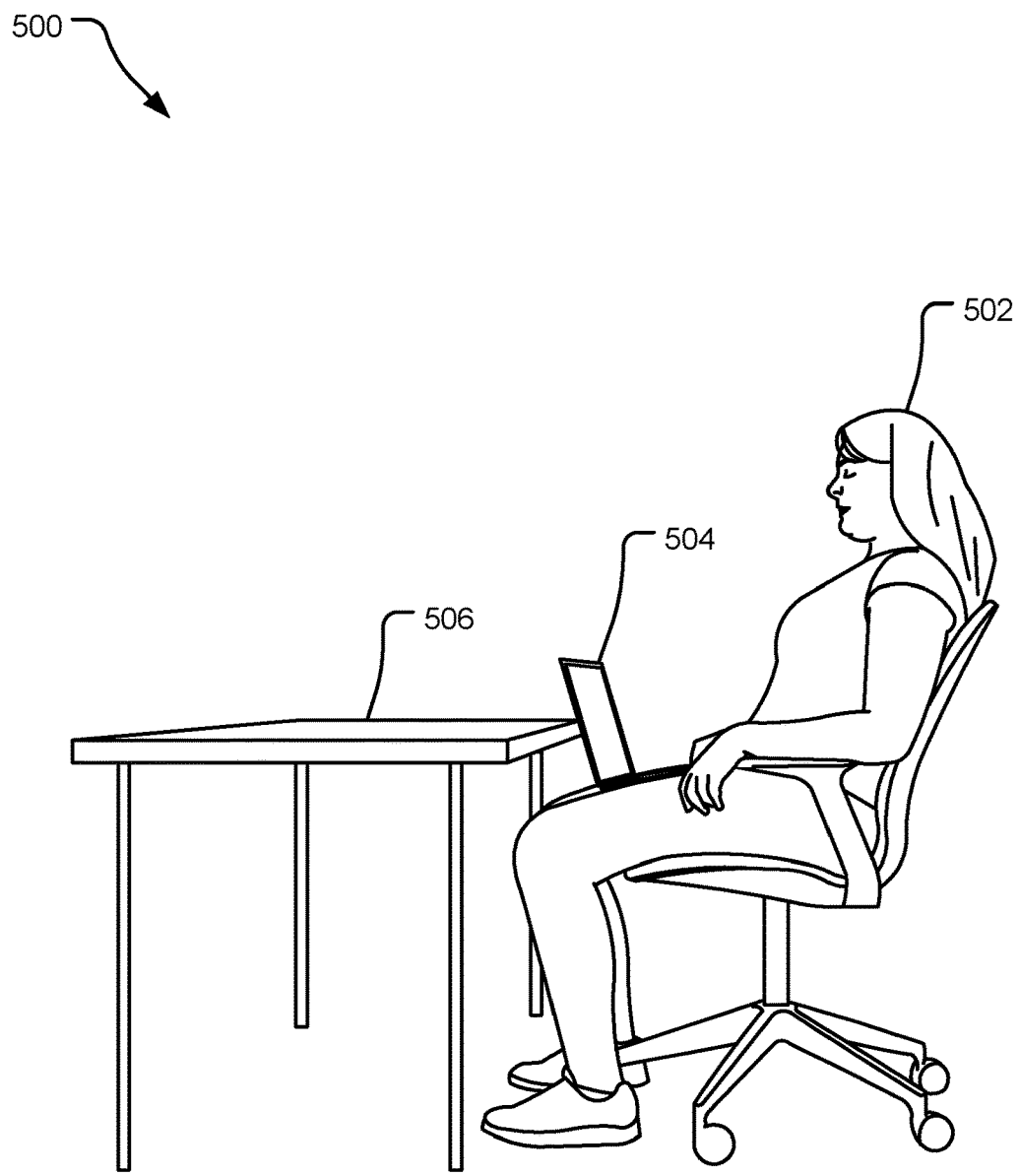
FIG. 5 illustrates yet another example use case of a motion sensor.

FIG. 5 illustrates yet another example use case 500 of the motion sensor. The use case 500 shows a communication device 504, an inanimate surface 506, and a seated user 502. The communication device 504 may be an implementation of communication device 104. The communication device 504 does not rest on an inanimate surface but on the user's lap. In use case 500, despite the fact that the user 502 is not directly engaged with the communication device 504 by, for example, typing or scrolling, the user 502 engages the communication device 504 with the user's lap. In this use case 500, the communication device 504 and its motion sensor detect motion indicative of user interaction with the communication device 504 via the motions of the lap.

In FIGS. 4 and 5, a classifier classifies the detected motion as a SAR IN MOTION when compared with background noise attributable to elements of the communication device 404, 504 and the inanimate surface 406, 506. Consequently, the SAR management system of the communication device 404, 504 and/or a controller of the motion sensor may adjust transmitter power in the communication device 404, 504. if prior to use cases 400 and 500, one or more of the classification conditions and classification parameters had been adjusted to accommodate a SAR STATIONARY state, the classification conditions and classification parameters may be further adjusted to accommodate a SAR IN MOTION state. In these use cases 400, 500, a controller may increase sensitivity to motion in order to focus on the minor differences in motion attributable to human interaction with the communication device. A threshold may need to be correspondingly increased depending on the circumstances. Other tunable classification parameters and/or classification conditions may be adjusted to better determine the SAR motion state. Also, motion profiles may be assessed for each of the use cases 400, 500. For example, the use case 400 may be identified as a communication device on an inanimate surface with a user engagement motion profile. Similarly, the use case 500 may be flagged as a communication device on the user's lap with no active user engagement motion profile.

Figure 6:
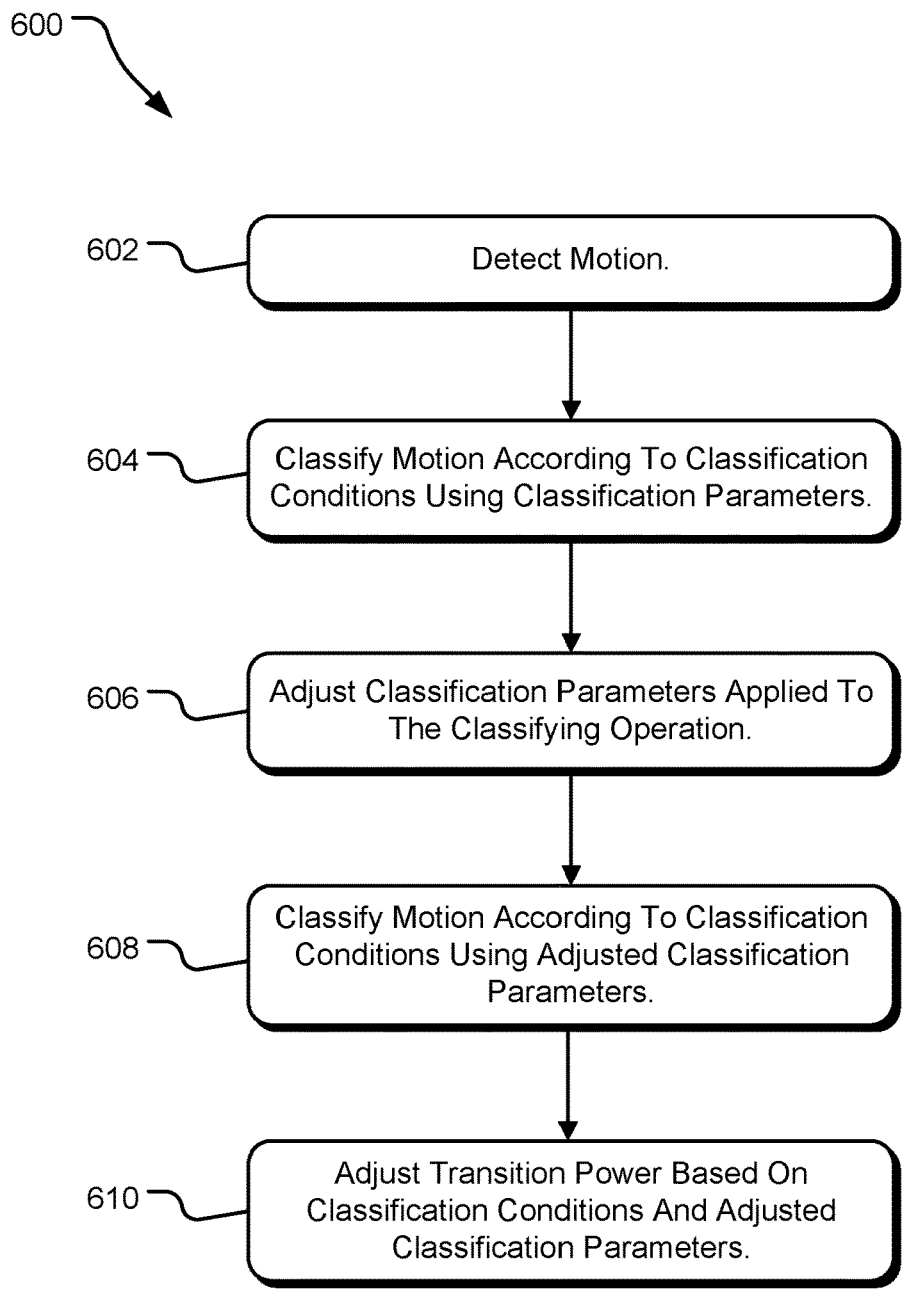
FIG. 6 illustrates example operations for using a motion sensor.

FIG. 6 illustrates example operations 600 of use of a motion sensor. A detection operation 602 detects motion. Detection operation 602 may use a motion detector of a motion sensor to detect the motion. The motion sensor may have signal processing elements, for example, one or more of a sampler, a frequency renderer, a signal discriminator, and a smoother. As such, the detection operation 602 may optionally have a sampling operation that samples detected motion to produce a discrete detected motion signal. The sampler may have a sample rate which may be a tunable classification parameter.

The detection operation 602 may use a frequency renderer to render sampled motions detected into a frequency domain signal from a time/sample domain signal. Implementations exist where rendering the signal in a frequency domain representation is unnecessary, such that the motion sensor can operate on frequency domain elements using the time-domain signal.

The detection operation 602 may optionally have a signal discriminating operation that removes particular frequencies or frequency ranges from a signal representing the detected motion. The frequencies or frequency ranges removed may be a tunable classification parameter. The signal discriminator may be, for example, one or more of a high pass filter, low pass filter, bandpass filter, digital software filter. The signal discriminator may be tunable to exclude frequencies likely indicative of background motion and include frequencies indicative of motion representing likely user interaction with the communication device.

The detection operation 602 may optionally have a smoothing operation that uses a smoother to smooth the signal. The smoother may help to reduce the effect of outliers and/or noise in the signal representing the detected motion. The smoother may render the signal into an energy representation. The smoother may use a mean square or root mean square average for smoothing energy representation of consecutive or otherwise related samples. For example, the motion detector may demonstrate detected motion in more than one axis (e.g., x, y, and z axes from a particular reference). A direction-independent magnitude of the energy in the signals for each sample can be determined by taking the square of the signal representing detected in each coordinate and summing them. This can be seen in equation 1, described above. The smoother may use a mean-squared function or a root-mean-squared function to smooth the direction-independent magnitude of energy in the signal over a variable window. An example of a mean squared representation is shown in equation (2). An example of a root-mean-squared representation is shown in equation (3).

The detection operation 602 may have a sensitivity tuning operation that uses a sensitivity tuner to vary the sensitivity of the motion sensor to a detected motion. The sensitivity to motion may be a tunable classification parameter. In an implementation, the sensitivity may be modified by giving different weight to elements of the signal, for example, different weight to certain frequencies in the signal representing the detected motion, to certain samples (e.g., more recent samples) in the signal representing the detected motion, other elements of the signal representing the detected motion. The motion detector may be tuned to provide an output to a classifier of a controller.

Classifying operation 604 classifies detected motion according to one or more classification conditions using one or more tunable parameters. Some (perhaps not yet adjusted) tunable classification parameters may have been applied at the detection operation 602. In the classifying operation 604, the controller may receive the output of the motion detector and classify, using a classifier, the detected motion. The classifier may classify the detected motion by assessing the output of the detection operation 602 according to classification conditions.

In an implementation, the controller may include a tunable classification parameter that is a threshold to which the output of a sensitivity tuner and/or the detected motion is compared. The threshold may be a magnitude threshold, for example, a magnitude of signal energy to which the signal representing the magnitude of the detected motion is compared. The magnitude of the energy to be compared to the threshold may be the mean squared or root mean squared output of the smoother or may include a sample-by-sample comparison. The threshold may be an element of or responsive to a motion profile. Classifying operation 604 may compare the output of the detection operation 602 to the threshold in order to classify the detected motion as being in a SAR motion state. The comparison may be a classification condition.

In another implementation, the classification condition may be a comparison of magnitudes of individual frequency components rather than an overall magnitude of the signal energy. For example, magnitudes of certain frequencies can be compared with respect to expected motion profiles to determine a most likely motion profile that corresponds to the distribution of magnitudes of energy of the signal at different frequencies. When a user interacts with the communication device, the motion detector may be able to detect motions specific to a human body, for example, one or more of cardiovascular heartbeat, pulse, other measures of blood flow, or other natural human motions. Detection of a process indicating user interaction, even if it is small in magnitude, may be sufficient to trigger a SAR IN MOTION state classification The controller may itself classify a detected motion according to a classification condition (e.g., a SAR motion state) or may indicate as much to a monitoring service of the communication device to classify the SAR motion state. For example, the monitoring service may take as input the outputs of more than one controller of the plurality of motion sensors to classify a SAR motion state and, correspondingly, determine whether transmission power needs to be backed off or may be increased.

An implementation of a classification condition used in the classifying operation may be a comparison of a Mean Ratio with a threshold value. A mean ratio may be calculated using equation 4. The threshold value for the Mean Ratio may vary depending on circumstances, for example, one or more of a sensitivity to motion (where recent sample energies or other elements of the signal may receive greater weight relative to other elements), a motion profile representing the expected type of motion detected. Implementations of the Mean Ratio may include, for example, ratios of 1.2, 1.3, 1.4, 1.5, 1.6, 1.7, 1.8, 1.9, 2, 2.1, 2.2, 2.3, 2.4, 2.5, 2.6, or 2.7 or may be in ranges of Mean Ratios, for example ranges 1.2-2, 1.2-2.5, 1.8-2.2, 1.9-2.1.

The classifying operation 604 may also maintain the SAR IN MOTION state for a period of time, perhaps a decay interval. A decay interval is a period of time or corresponding samples over which the SAR IN MOTION state remains triggered based on the detected motion continuing to indicate SAR IN MOTION. The decay interval may require a certain time frame or a number of samples over which the detected motion indicates no user interaction motion before a SAR IN MOTION state is no longer triggered. In an implementation, a decay interval may require 15 seconds or 15 samples where a classification condition (e.g., threshold) is not met, indicating the device is experiencing only background motion indicating a SAR STATIONARY state. The decay interval over which a SAR motion state is maintained may be based at least in part on the detected motion.

In implementations, the motion sensor may have elements that malfunction and/or fail to report results as expected. These may trigger the classifying operation 604 to trigger a sensor failure state in the controller of the communication device. In a sensor failure state, the communication device may default to transmission power indicative of a SAR IN MOTION state to be safe. Implementations may further have a sensor sleep state. If no subscription is active, the classifying operation 604 may cause the controller or SAR manager may default to a SAR safety state while the SAR motion framework is in sleep states.

Adjusting operation 606 adjusts one or more classification parameters applied to the classifying operation. The adjusting operation 606 may be responsive to the classifying operation 604. When a controller has classified according to a classification condition, the controller may responsively adjust one or more of the classification parameters based on whether the detected motion has been classified according to the classification conditions as being in a particular SAR motion state. The controller may further responsively adjust the one or more classification conditions responsive to the satisfaction of the one or more classification conditions, based on one or more of the satisfaction of the one or more classification conditions and any adjustments made to the classification parameters. For example, in an implementation, if the controller has determined over prior samples that the motion sensor (and/or communication device) is in a SAR STATIONARY state, a next detected motion sample may be sufficient (e.g., yield a signal of sufficient energy magnitude) to satisfy a classification condition (e.g., exceed a threshold), such that the device is determined to likely be in a SAR IN MOTION state. The controller may focus more on the motion by tuning elements of the motion sensor.

The adjusting operation 606 may adjust the threshold to better focus the detection of the motion. The threshold may also be dynamic if certain signal elements are emphasized or omitted, perhaps based on a motion profile. For example, if the magnitude of more recent samples is increased for emphasis, the magnitude of the threshold may need to be correspondingly increased in order to account for the artificial increase in signal energy. Another example may be that the threshold needs to be reduced when certain frequencies are omitted to account for the expected loss of energy in the excluded elements. A basis for comparison of whether detected motion represents SAR IN MOTION state user interaction motion or SAR STATIONARY state background motion may be a noise floor.

The adjusting operation 606 may alternatively or additionally adjust the threshold in order to accommodate artificial increases in the signal energy to increase sensitivity or to better account for particular motion profiles. The threshold may be decreased in order to accommodate artificial decreases in the signal energy (e.g., excluding signal energy of certain excluded signal elements) to decrease sensitivity or to better account for particular motion profiles. If the Mean Ratio exceeds the threshold (i.e., satisfies a classification condition to show SAR IN MOTION), the motion sensor 114 may determine the motion detected represents user interaction with the communication device 104. The motion sensor 114 may, on its own, one or more of trigger the SAR motion state and adjust the transmission power of the communication device 104. Alternatively or additionally, the motion sensor 114 may transmit the output of the Mean Ratio comparison to the threshold to an element of the communication device 104 to allow the communication device 104 to determine or classify, perhaps in concert with other outputs of other motion sensors 114, one or more of a SAR motion state, power transmission adjustment instructions, and a relevant or appropriate motion profile corresponding to a pattern of activity associated with the detected motion(s). It should be appreciated that if a decision is made by the controller or another element of the communication device to tune the motion sensor to better distinguish from background noise, the threshold may be dynamically changed to account for the increased sensitivity. The motion sensor may adjust the one or more motion classification parameters based at least in part on a predefined motion profile The adjusting operation 606 may alternatively or additionally modify the sample rate to get a more or less precise reading of the motion detected. The sampler may increase the sampling rate in order to better focus on the detected motion, perhaps to allow for precise detection of when a user is no longer engaged with the communication device and allow for a quicker transition to a SAR STATIONARY state. The sample rate may be decreased in some circumstances, for example, when a sufficient period (perhaps a decay interval) has passed in which the detected motion no longer indicates that a user is engaged with the communication device 204 such that the classification condition transitions the SAR Motion state from a SAR IN MOTION state to a SAR STATIONARY state.

The adjusting operation 606 may alternatively or additionally expand or narrow a variable window in order to adjust the smoothness of the representation of the signal magnitude for comparison. The number of samples in the variable window may be a tunable classification parameter to adjust the sensitivity to the detected motion. Examples of numbers and ranges of numbers of samples in a variable window include 20 samples, 200 samples, at least 20 samples, at least 200 samples, and between 20 and 200 samples. The variable window may be narrowed to include fewer samples when, for example, a classifier of the controller classifies a detected motion as indicative of a SAR IN MOTION STATE. This narrowing of the field may give more resolution to the signal. The variable window may be expanded to include more samples or a smaller time frame when, for example, a classifier of the controller classifies a detected motion as indicative of a SAR STATIONARY state.

The controller may alternatively or additionally modify the decay interval, perhaps requiring more or fewer samples indicating a SAR STATIONARY state before transitioning from a SAR IN MOTION state to a SAR STATIONARY state. The decay interval may be increased if the detected motion indicates there has been a longer or more pronounced pattern of user engagement with the communication device. The decay interval may be decreased if the detected motion indicates that there has been no or a short or less pronounced pattern of user engagement with the communication device.

The adjusting operation 606 may adjust the sensitivity by giving different weights to samples and/or frequency elements in the samples. For example, if a SAR IN MOTION state is triggered, greater weight may be given to more recent samples and/or to frequency elements likely representing human interaction.

The classifying operation 608 classifies the detected motion according to the one or more motion classification conditions using the one or more adjusted motion classification parameters. The classifying operation 608 may be an implementation of classifying operation 604, except the input to classifying operation 608 is based on the adjusted classification parameters adjusted in the adjusting operation 606. Classifying operation 608 may similarly compare a signal representing the detected motion having been tuned by classification parameters adjusted in the adjusting operation 606 to one or more of a magnitude threshold, to magnitude thresholds of certain frequencies, to motion profiles, to the distribution of magnitudes of energy of the signal at different frequencies, and to motions specific to a human body, and any other comparisons expressed herein. The classifying operation 608 may also, similarly to classifying operation 604, maintain the SAR IN MOTION state for a period of time, perhaps a decay interval.

Adjusting operation 610 is adjusting the transmission power based on one or more motion classification conditions and one or more adjusted motion classification parameters using the one or more adjusted motion classification parameters. In an implementation, the adjusting operation 610 may be responsive to the classifying operation 608. Depending on whether classifying operation 608 classifies the detected motion as indicating a SAR IN MOTION STATE or a SAR STATIONARY state, the power provided to the transmitters in the communication device may be adjusted by one or more of a controller in the motion sensor or a SAR manager in the communication device. For example, if the classifying operation 608 represents a transition from a SAR IN MOTION state to a SAR STATIONARY state, the transmission power supplied to the transmitters may be increased. If the classifying operation 608 represents a transition from a SAR STATIONARY state to a SAR IN MOTION state, the transmission power to the transmitters may be decreased.

In implementations, the motion sensor may be in communication with a SAR manager, perhaps by means of a platform sensor application programming interface. Depending on the capabilities of the platform, the motion sensor may be part of a default sensor stack, or a platform environment may provide an original equipment manufacturer the ability to create a custom sensor that can be accessed like a regular sensor via the platform sensor API.

The controller or SAR manager may include or be in communication with the power adjuster responsible for adjusting the transmission power of the communication device. The power adjuster may adjust the power based at least in part on one or more motion classification conditions and one or more adjusted motion classification parameters, responsive to the operation of classifying using the one or more adjusted motion classification parameters. The transmission power may be reduced when the communication device switches to a SAR IN MOTION state and may be increased when the communication device switches to a SAR STATIONARY state.

In an implementation, each of the operations 600 of the method shown in FIG. 6 is a distinct operation. In another implementation, although depicted as distinct operations in FIG. 6, operations 602-610 may not be distinct operations. In other implementations, the method may not have all of the above operations and/or may have other operations in addition to or instead of those listed above. The operations 600 of the method shown in FIG. 6 may be performed in another order. Subsets of the operations listed above as part of the method shown in FIG. 6 may be used to form their own method. The operations 600 of the method may be repeated in any combination and order any number of times, for example, continuously or selectively looping in order to dynamically activate SAR motion states and corresponding transmission powers.

Figure 7:
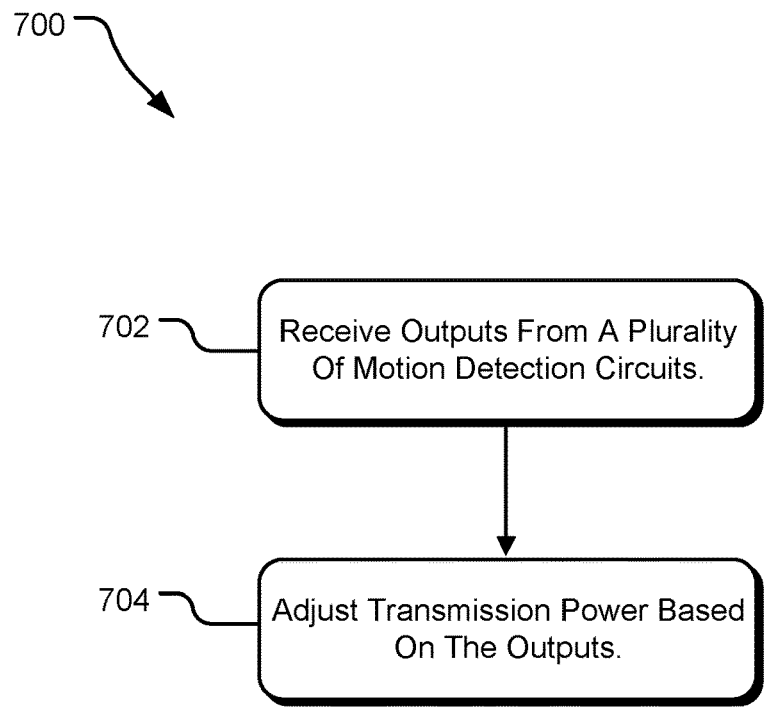
FIG. 7 illustrates example operations for using a plurality of motion sensors in a communication device.

FIG. 7 illustrates example operations 700 for use of a plurality of motion sensors in a communication device. A receiving operation 702 receives outputs from a plurality of motion sensors. In implementations, the plurality of motion sensors may be located in different positions of the communication device, for example, locations distant from internal components that cause background motion or proximal to electronics transmitters. The outputs may come in the form of a localized classification of a SAR motion state, a satisfaction or failure to satisfy one or more classification conditions, adjustments to one or more of the one or more classification parameters and the one or more classification conditions, and any other output of the controller and/or motion sensor described herein.

In implementations, each motion sensor may be in communication with a SAR manager, perhaps by means of a platform sensor application programming interface. Depending on the capabilities of the platform, the motion sensor may be part of a default sensor stack or a platform environment may provide an original equipment manufacturer the ability to create a custom sensor that can be accessed like a regular sensor via the platform sensor API. The SAR manager may collect the outputs of the plurality of motion sensors to determine an overall profile of motion corresponding to a specific pattern of user interaction or non-interaction.

An adjusting operation 704 adjusts the transmission power of the communication device based on the outputs. The adjusting operation 704 may use a SAR manager to collect the outputs and determine whether the communication device is in a SAR IN MOTION state based on the outputs. This may be accomplished by a SAR manager stored in the memory of the communication device and executed by a processor of the communication device. The SAR manager may be represented by a set of predetermined tables or may be more dynamic using machine learning or other inferential algorithms. The adjusting operation 704 may further adjust transmission power based on the determined SAR motion state. After a decay interval over which the SAR manager determines there is no SAR IN MOTION state, the adjusting operation 704 may include increasing power to a higher or maximum level to improve transmission performance. The controller or SAR manager may include or be in communication with the power adjuster responsible for adjusting the transmission power of the communication device. The power adjuster may adjust the power based at least in part on one or more motion classification conditions and one or more adjusted motion classification parameters, responsive to the operation of classifying using the one or more adjusted motion classification parameters.

In implementations, the motion sensor may have elements that are not working appropriately and/or fail to report results as expected. These may trigger the adjusting operation 704 to flag a sensor failure state in the controller of the communication device. In a sensor failure state, the communication device may default to transmission power indicative of a SAR IN MOTION state to be safe. Implementations may further have a sensor sleep state. If no subscription is active, the controller or SAR manager may default to a SAR safety state while the SAR motion framework is in sleep states.

In an implementation, each of the operations 700 of the method shown in FIG. 7 is a distinct operation. In another implementation, although depicted as distinct operations in FIG. 7, operations 702-704 may not be distinct operations. In other implementations, the method shown in FIG. 7 may not have all of the above operations and/or may have other operations in addition to or instead of those listed above. The operations 700 of the method shown in FIG. 7 may be performed in another order. Subsets of the operations listed above as part of the method shown in FIG. 7 may be used to form their own method. The operations 700 of the method may be repeated in any combination and order any number of times, for example, continuously or selectively looping, in order to dynamically determine SAR motion states and corresponding transmission powers.

Figure 8:
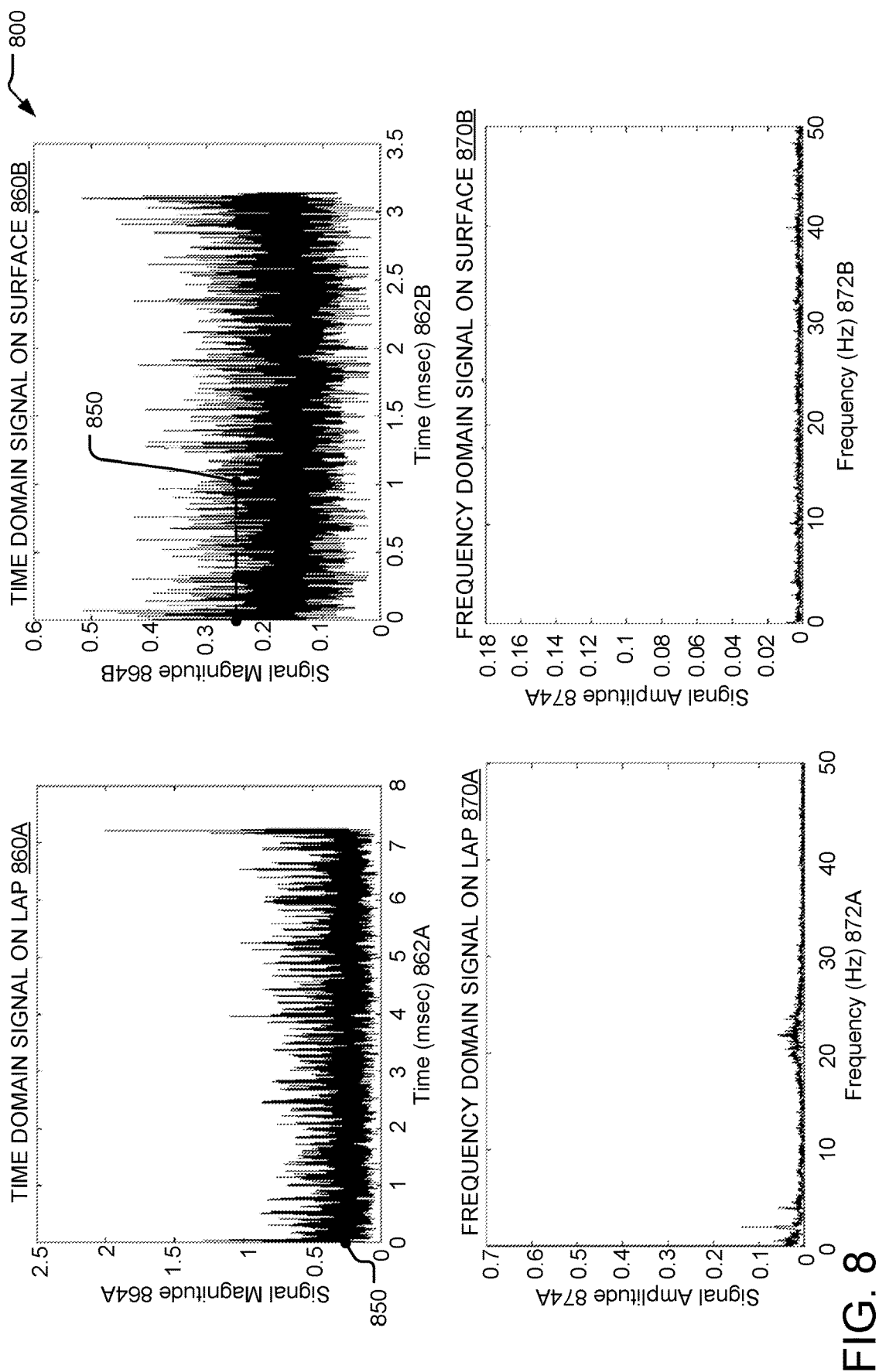
FIG. 8 illustrates an example comparison between SAR IN MOTION and SAR STATIONARY states.

FIG. 8 illustrates an example comparison between SAR IN MOTION and SAR STATIONARY states 800. Graphs 860A and 860B represent time-domain signals of detected motion for scenarios where the communication device is on a lap and where the communication device is on an inanimate surface, respectively. Graphs 870A and 870B are frequency domain representations of elements of 860A and 860B, respectively.

In graphs 860A and 860B, it can be seen that an absolute threshold is applied over an average of samples, the threshold in this example being about 0.25. The classification condition considered is a comparison of the magnitude of the detected motion with the threshold. This may appear different in the graphs 860A and 860B, but graphs 860A and 860B have different scales. The graphs 860B and 870B may represent a noise floor indicative of background motion.

The graph 860A includes an ordinate axis 862A, representing time in seconds, and an abscissa axis 864A, representing detected motion signal magnitude. An average threshold 850 over a given time is shown to be about 0.25. While the data looks to have elements above and below the threshold, the data over the relevant averaging period has a value of 0.2977. This average value exceeds the average threshold 850 of about 0.25. Therefore, a controller motion is represented in graph 860A as indicating a SAR IN MOTION state of a communication device on a lap. The communication device, whether by the controller or other elements of the communication device, may determine to backoff power in response to determining a SAR IN MOTION state as in the graph 860A.

The graph 860B includes an ordinate axis 862B, representing time in seconds, and an abscissa axis 864B, representing detected motion signal magnitude. An average threshold 850 over a given time is shown to be about 0.25. While the data looks to have elements above and below the threshold, the average of the signal data over the relevant averaging period has a value of 0.1667. This average value is lower than the average threshold 850 of about 0.25. Therefore, a controller would classify the motion represented in graph 860B as indicating a SAR STATIONARY state of a communication device on an inanimate surface. The communication device, whether by the controller or other elements of the communication device, may determine to maintain or increase transmission power in response to determining a SAR STATIONARY state as in the graph 860B.

Graphs 870A and 870B are presented in the frequency domain. Graph 870A includes an ordinate axis, 872A, representing frequency in Hz of the signal of detected motion, and an abscissa axis 874A, representing the amplitude of specific frequency elements. Graph 870B includes an ordinate axis 872B, representing frequency in Hz of the signal of detected motion, and an abscissa axis 874B, representing the amplitude of specific frequency elements. As can be seen by comparison of 870A and 870B, the human interaction of a lap engaging the communication device provides higher amplitudes of certain frequencies representing the engagement. For example, the spikes seen in the 0-5 Hz range and in the 17-32 Hz range of the graph 870A that are not present in the graph 870B can be distinguished as potential human interaction motion. A controller of the motion sensor may determine the detected motion based on amplitudes at human-interaction-relevant frequencies indicate human interaction with the communication device and may classify the detected motion as indicating a SAR IN MOTION state. The communication device, whether by the controller or other elements of the communication device, may determine to backoff power in response to determining a SAR IN MOTION state as in the graph 870A. Contrarily, if the controller detects motion as in the graph 870B, the controller may classify the detected motion as indicating a SAR STATIONARY state. The communication device, whether by the controller or other elements of the communication device, may determine to maintain or increase transmission power in response to determining a SAR STATIONARY state as in the graph 870B.

Figure 9:
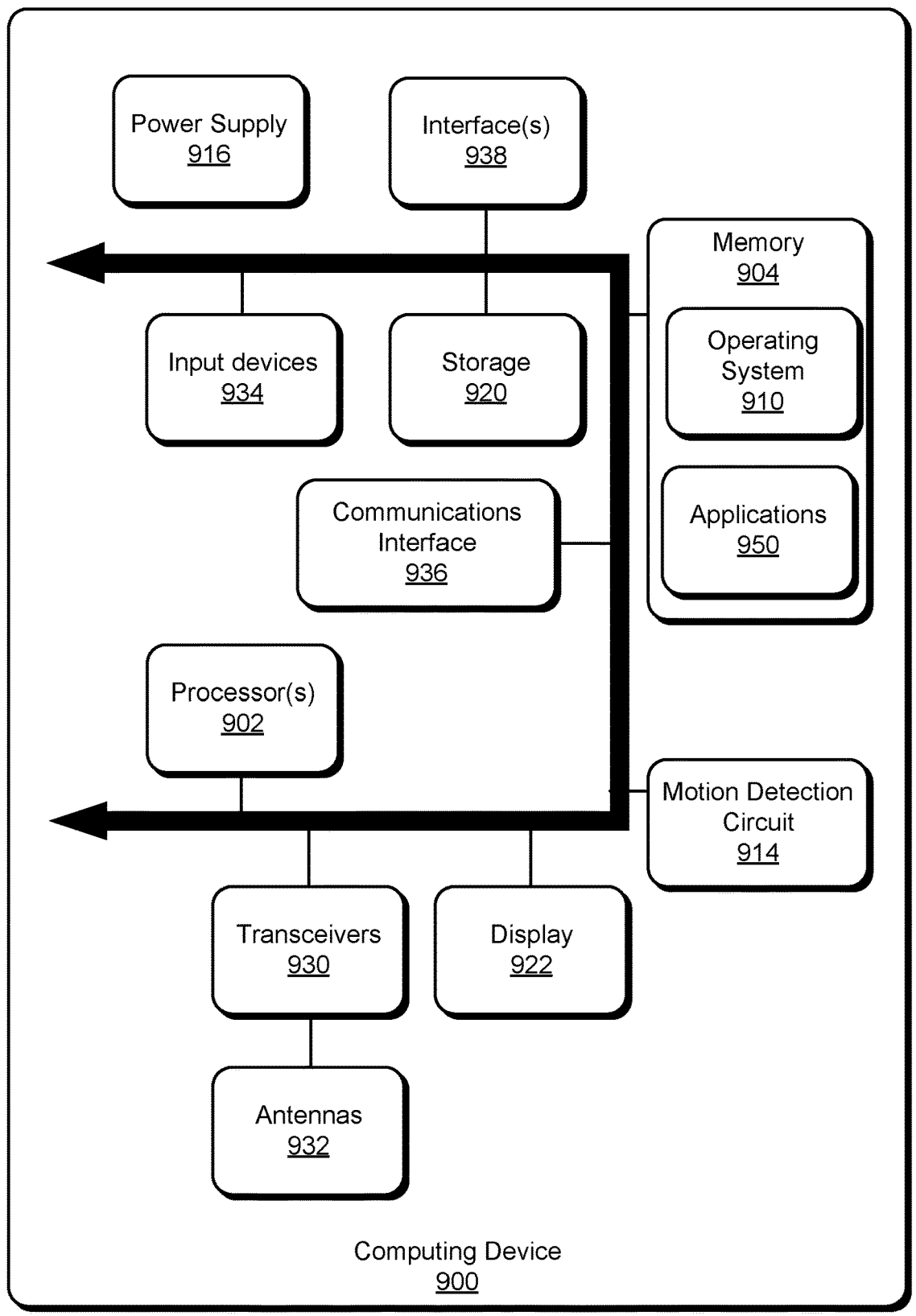
FIG. 9 illustrates an example communication device for implementing the features and operations of the described technology.

The controller may further adjust classification parameters depending on the classification. For example, if a motion indicative of SAR IN MOTION states is detected, the sensitivity of a sensitivity tuner may be adjusted to further hone in on whether the motion is SAR motion. The threshold may be correspondingly adjusted to account for any artificial change in signal energy due to tuning of the motion sensor. The motion sensor may adjust the one or more motion classification parameters based at least in part on the predefined motion profile FIG. 9 illustrates an example communication device 900 for implementing the features and operations of the described technology. The communication device 900 may embody a remote-control device or a physical controlled device and is an example network-connected and/or network-capable device and may be a client device, such as a laptop, mobile device, desktop, tablet; a server/cloud device; an internet-of-things device; an electronic accessory; or another electronic device. The communication device 900 includes one or more processor(s) 902 and a memory 904. The memory 904 generally includes both volatile memory (e.g., RAM) and nonvolatile memory (e.g., flash memory). An operating system 910 resides in the memory 904 and is executed by the processor(s) 902. The communication device 900 may be an implementation of communication device 104. The communication device may also have one or more motion sensors 914.

In an example communication device 900, as shown in FIG. 9, one or more modules or segments, such as applications 950, a SAR management API, a SAR manager, machine, learning algorithms, SAR motion frameworks, motion detectors, classifiers, parameter adjusters, samplers, signal discriminators, smoothers, signal processors, sensitivity tuners, controllers, transmission power adjusters, transmitters, and inferential algorithms are loaded into the operating system 910 on the memory 904 and/or storage 920 and executed by processor(s) 902. The storage 920 may include one or more tangible storage media devices and may store SAR motion profiles, SAR motion states, SAR management protocols, SAR instructions, SAR backoff instructions, power transmission adjustment instructions, machine learning algorithms, SAR motion tables, transmission power management tables, classification parameters, classification conditions, controller outputs, thresholds, discriminated frequencies, sample numbers, sensitivity tunings, decay intervals, frequencies indicating user interaction, inferential algorithms, frequencies indicating background motion, locally and globally unique identifiers, requests, responses, and other data and be local to the communication device 900 or may be remote and communicatively connected to the communication device 900.

The communication device 900 includes a power supply 916, which is powered by one or more batteries or other power sources and which provides power to other components of the communication device 900. The power supply 916 may also be connected to an external power source that overrides or recharges the built-in batteries or other power sources.

The communication device 900 may include one or more communication transceivers 930, which may be connected to one or more antenna(s) 932 to provide network connectivity (e.g., mobile phone network, Wi-Fi®, Bluetooth®) to one or more other servers and/or client devices (e.g., mobile devices, desktop computers, or laptop computers). The communication device 900 may further include a network adapter 936, which is a type of communication device. The communication device 900 may use the adapter and any other types of communication devices for establishing connections over a wide-area network (WAN) or local-area network (LAN). It should be appreciated that the network connections shown are examples and that other communication devices and means for establishing a communications link between the communication device 900 and other devices may be used.

The communication device 900 may include one or more input devices 934 such that a user may enter commands and information (e.g., a keyboard or mouse). These and other input devices may be coupled to the server by one or more interfaces 938, such as a serial port interface, parallel port, or universal serial bus (USB). The communication device 900 may further include a display 922, such as a touch screen display.

The communication device 900 may include a variety of tangible processor-readable storage media and intangible processor-readable communication signals. Tangible processor-readable storage can be embodied by any available media that can be accessed by the communication device 900 and includes both volatile and nonvolatile storage media, removable and non-removable storage media. Tangible processor-readable storage media excludes communications signals (e.g., signals per se) and includes volatile and nonvolatile, removable and non-removable storage media implemented in any method or technology for storage of information such as processor-readable instructions, data structures, program modules, or other data. Tangible processor-readable storage media includes, but is not limited to, RAM, ROM, EEPROM, flash memory or other memory technology, CDROM, digital versatile disks (DVD) or other optical disk storage, magnetic cassettes, magnetic tape, magnetic disk storage or other magnetic storage devices, or any other tangible medium which can be used to store the desired information and which can be accessed by the communication device 900. In contrast to tangible processor-readable storage media, intangible processor-readable communication signals may embody processor-readable instructions, data structures, program modules, or other data resident in a modulated data signal, such as a carrier wave or other signal transport mechanism. The term "modulated data signal" means a signal that has one or more of its characteristics set or changed in such a manner as to encode information in the signal. By way of example, and not limitation, intangible communication signals include signals traveling through wired media such as a wired network or direct-wired connection, and wireless media such as acoustic, RF, infrared, and other wireless media.

Various software components described herein are executable by one or more processors, which may include logic machines configured to execute hardware or firmware instructions. For example, the processors may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Aspects of processors and storage may be integrated together into one or more hardware logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of a remote-control device and/or a physical controlled device implemented to perform a particular function. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

It will be appreciated that a "service," as used herein, is an application program executable across one or multiple user sessions. A service may be available to one or more system components, programs, and/or other services. In some implementations, a service may run on one or more server computing devices.

The logical operations making up embodiments described herein may be referred to variously as operations, steps, objects, or modules. Furthermore, it should be understood that logical operations may be performed in any order, adding or omitting operations as desired, regardless of whether operations are labeled or identified as optional, unless explicitly claimed otherwise or a specific order is inherently necessitated by the claim language. While this specification contains many specific implementation details, these should not be construed as limitations on the scope of any inventions or of what may be claimed, but rather as descriptions of features specific to particular implementations of the particular described technology. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

An example method of managing transmission power of a communication device including detecting motion of the communication device using a motion sensor, classifying detected motion according to one or more motion classification conditions using one or more motion classification parameters, adjusting the one or more motion classification parameters applied to the classifying operation, responsive to the classifying operation, classifying the detected motion according to the one or more motion classification conditions using the one or more adjusted motion classification parameters, and adjusting the transmission power of the communication device based at least in part on the one or more motion classification conditions and the one or more adjusted motion classification parameters, responsive to the operation of classifying using the one or more adjusted motion classification parameters.

Another example method of any preceding method is provided, wherein the one or more motion classification conditions classify whether the detected motion indicates a SAR IN MOTION state that represents user interaction with the communication device.

Another example method of any preceding method is provided, wherein the one or more motion classification conditions classify whether the detected motion indicates a predefined motion profile representative of a particular pattern of user interaction with the communication device.

Another example method of any preceding method is provided, wherein the operation of adjusting the one or more motion classification parameters includes adjusting the one or more motion classification parameters based at least in part on the predefined motion profile.

Another example method of any preceding method is provided, wherein the operation of classifying detected motion according to one or more motion classification conditions using one or more motion classification parameters includes measuring a magnitude of a signal representing frequencies detected in the detected motion that represent human interaction and comparing the magnitude of the signal to a predetermined threshold.

Another example method of any preceding method is provided, wherein the operation of adjusting the one or more motion classification parameters includes adjusting a sensitivity to the detected motion.

Another example method of any preceding method is provided, wherein the operation of adjusting the one or more motion classification parameters comprises an operation of adjusting one or more of a sample rate at which the detected motion is sampled, a decay interval over which a SAR motion state based at least in part on the detected motion is maintained, a threshold to which the detected motion is compared, a motion profile to which the detected motion is compared, and a variable window over which the detected motion is classified in the classifying operation.

An example communication device having a processor and a memory is provided. The processor is configured to execute operations stored in the memory. The communication device includes a motion detector operable to detect motion of the communication device using a motion detection sensor, a classifier executable by the processor and operable to classify detected motion according to one or more motion classification conditions using one or more motion classification parameters, a parameter adjuster executable by the processor and operable to adjust the one or more motion classification parameters applied to the classification, responsive to the classification, a transmission power adjuster executable by the processor and operable to adjust the transmission power of the communication device based at least in part on the one or more motion classification conditions and the one or more adjusted motion classification parameters, responsive to the classification using the one or more adjusted motion classification parameters. The classifier is further operable to classify the detected motion according to the one or more motion classification conditions using the one or more adjusted motion classification parameters.

Another example communication device of any preceding device, wherein the one or more motion classification conditions are usable to classify whether the detected motion indicates a SAR IN MOTION state that represents user interaction with the communication device.

Another example communication device of any preceding device, wherein the one or more motion classification conditions are usable to classify whether the detected motion indicates a predefined motion profile representative of a particular pattern of user interaction with the communication device.

Another example communication device of any preceding device, wherein the parameter adjuster is operable to adjust the one or more motion classification parameters based at least in part on the predefined motion profile.

Another example communication device of any preceding device, wherein the classifier is operable to measure a magnitude of a signal representing frequencies detected in the detected motion that represent human interaction and compare the magnitude of the signal to a predetermined threshold.

Another example communication device of any preceding device, wherein the parameter adjuster is operable to adjust a sensitivity to the detected motion.

Another example communication device of any preceding device, wherein the parameter adjuster is operable to adjust one or more of a sample rate at which the detected motion is sampled, a decay interval over which a SAR motion state based at least in part on the detected motion is maintained, a threshold to which the detected motion is compared, a motion profile to which the detected motion is compared, and a variable window over which the detected motion is classified in the classification.

One or more example tangible processor-readable storage media embodied with instructions for executing on one or more processors and circuits of a communication device a process for adjusting transmission power is provided. The process includes detecting motion of the communication device using a motion sensor, classifying detected motion according to one or more motion classification conditions using one or more motion classification parameters, adjusting the one or more motion classification parameters applied to the classifying operation, responsive to the classifying operation, classifying the detected motion according to the one or more motion classification conditions using the one or more adjusted motion classification parameters, and adjusting the transmission power based at least in part on the one or more motion classification conditions and the one or more adjusted motion classification parameters, responsive to the operation of classifying using the one or more adjusted motion classification parameters.

One or more other example tangible processor-readable storage media of any preceding media is provided, wherein the one or more motion classification conditions are usable to classify whether the detected motion indicates a SAR IN MOTION state that represents user interaction with the communication device.

One or more other example tangible processor-readable storage media of any preceding media is provided, wherein the one or more motion classification conditions are usable to classify whether the detected motion indicates a predefined motion profile representative of a particular pattern of user interaction with the communication device.

One or more other example tangible processor-readable storage media of any preceding media is provided, wherein the operation of adjusting the one or more motion classification parameters comprises adjusting the one or more motion classification parameters based at least in part on the predefined motion profile.

One or more other example tangible processor-readable storage media of any preceding media is provided, wherein the operation of classifying detected motion according to one or more motion classification conditions using one or more motion classification parameters comprises measuring a magnitude of a signal representing frequencies detected in the detected motion that represent human interaction and comparing the magnitude of the signal to a predetermined threshold.

One or more other example tangible processor-readable storage media of any preceding media is provided, wherein the operation of adjusting the one or more motion classification parameters comprises an operation of adjusting one or more of a sample rate at which the detected motion is sampled, a decay interval over which a SAR motion state based at least in part on the detected motion is maintained, a threshold to which the detected motion is compared, a motion profile to which the detected motion is compared, and a variable window over which the detected motion is classified in the classifying operation.

An example system for managing transmission power of a communication device including means for detecting motion of the communication device using a motion sensor, means for classifying detected motion according to one or more motion classification conditions using one or more motion classification parameters, means for adjusting the one or more motion classification parameters applied to the classification, responsive to the classification, means for classifying the detected motion according to the one or more motion classification conditions using the one or more adjusted motion classification parameters, and means for adjusting the transmission power of the communication device based at least in part on the one or more motion classification conditions and the one or more adjusted motion classification parameters, responsive to the classification using the one or more adjusted motion classification parameters.

Another example system of any preceding system is provided, wherein the one or more motion classification conditions classify whether the detected motion indicates a SAR IN MOTION state that represents user interaction with the communication device.

Another example system of any preceding system is provided, wherein the one or more motion classification conditions classify whether the detected motion indicates a predefined motion profile representative of a particular pattern of user interaction with the communication device.

Another example system of any preceding system is provided, wherein the means for adjusting the one or more motion classification parameters includes means for adjusting the one or more motion classification parameters based at least in part on the predefined motion profile.

Another example system of any preceding system is provided, wherein the means for classifying detected motion according to one or more motion classification conditions using one or more motion classification parameters includes means for measuring a magnitude of a signal representing frequencies detected in the detected motion that represent human interaction and means for comparing the magnitude of the signal to a predetermined threshold.

Another example system of any preceding system is provided, wherein the means for adjusting the one or more motion classification parameters includes means for adjusting a sensitivity to the detected motion.

Another example system of any preceding system is provided, wherein the means for adjusting the one or more motion classification parameters comprises means for adjusting one or more of a sample rate at which the detected motion is sampled, a decay interval over which a SAR motion state based at least in part on the detected motion is maintained, a threshold to which the detected motion is compared, a motion profile to which the detected motion is compared, and a variable window over which the detected motion is classified in the classification.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

A number of implementations of the described technology have been described. Nevertheless, it will be understood that various modifications can be made without departing from the spirit and scope of the recited claims.

What is claimed is:

1. A method of managing transmission power of a communication device, comprising:
    detecting motion of the communication device using a motion sensor;
    classifying detected motion according to one or more motion classification conditions using one or more motion classification parameters;
    adjusting the one or more motion classification parameters applied to the classifying operation, responsive to the classifying operation;
    classifying the detected motion according to the one or more motion classification conditions using the one or more adjusted motion classification parameters; and
    adjusting the transmission power of the communication device based at least in part on the one or more motion classification conditions and the one or more adjusted motion classification parameters, responsive to the operation of classifying using the one or more adjusted motion classification parameters.

2. The method of claim 1, wherein the one or more motion classification conditions classify whether the detected motion indicates a SAR IN MOTION state that represents user interaction with the communication device.

3. The method of claim 1, wherein the one or more motion classification conditions classify whether the detected motion indicates a predefined motion profile representative of a particular pattern of user interaction with the communication device.

4. The method of claim 3, wherein the operation of adjusting the one or more motion classification parameters comprises:
    adjusting the one or more motion classification parameters based at least in part on the predefined motion profile.

5. The method of claim 3, wherein the operation of classifying detected motion according to one or more motion classification conditions using one or more motion classification parameters comprises:
    measuring a magnitude of a signal representing frequencies detected in the detected motion that represent human interaction; and
    comparing the magnitude of the signal to a predetermined threshold.

6. The method of claim 1, wherein the operation of adjusting the one or more motion classification parameters comprises:
    adjusting a sensitivity to the detected motion.

7. The method of claim 1, wherein the operation of adjusting the one or more motion classification parameters comprises an operation of adjusting one or more of:
    a sample rate at which the detected motion is sampled;
    a decay interval over which a SAR motion state based at least in part on the detected motion is maintained;
    a threshold to which the detected motion is compared;
    a motion profile to which the detected motion is compared; and
    a variable window over which the detected motion is classified in the classifying operation.

8. A communication device having a processor and a memory, the processor configured to execute operations stored in the memory, the communication device comprising:
    a motion detector operable to detect motion of the communication device using a motion detection sensor;
    a classifier executable by the processor and operable to classify detected motion according to one or more motion classification conditions using one or more motion classification parameters;
    a parameter adjuster executable by the processor and operable to adjust the one or more motion classification parameters applied to the classification, responsive to the classification; and
    a transmission power adjuster executable by the processor and operable to adjust the transmission power of the communication device based at least in part on the one or more motion classification conditions and the one or more adjusted motion classification parameters, responsive to the classification using the one or more adjusted motion classification parameters, the classifier being further operable to classify the detected motion according to the one or more motion classification conditions using the one or more adjusted motion classification parameters.

9. The communication device of claim 8, wherein the one or more motion classification conditions are usable to classify whether the detected motion indicates a SAR IN MOTION state that represents user interaction with the communication device.

10. The communication device of claim 8, wherein the one or more motion classification conditions are usable to classify whether the detected motion indicates a predefined motion profile representative of a particular pattern of user interaction with the communication device.

11. The communication device of claim 10, wherein the parameter adjuster is operable to adjust the one or more motion classification parameters based at least in part on the predefined motion profile.

12. The communication device of claim 10, wherein the classifier is operable to measure a magnitude of a signal representing frequencies detected in the detected motion that represent human interaction and compare the magnitude of the signal to a predetermined threshold.

13. The communication device of claim 8, wherein the parameter adjuster is operable to adjust a sensitivity to the detected motion.

14. The communication device of claim 8, wherein the parameter adjuster is operable to adjust one or more of:
    a sample rate at which the detected motion is sampled;
    a decay interval over which a SAR motion state based at least in part on the detected motion is maintained;
    a threshold to which the detected motion is compared;
    a motion profile to which the detected motion is compared; and
    a variable window over which the detected motion is classified in the classification.

15. One or more tangible processor-readable storage media embodied with instructions for executing on one or more processors and circuits of a communication device a process for adjusting transmission power, comprising:
    detecting motion of the communication device using a motion sensor;
    classifying detected motion according to one or more motion classification conditions using one or more motion classification parameters;

adjusting the one or more motion classification parameters applied to the classifying operation, responsive to the classifying operation;

classifying the detected motion according to the one or more motion classification conditions using the one or more adjusted motion classification parameters; and adjusting the transmission power based at least in part on the one or more motion classification conditions and the one or more adjusted motion classification parameters, responsive to the operation of classifying using the one or more adjusted motion classification parameters.

16. The one or more tangible processor-readable storage media of claim 15, wherein the one or more motion classification conditions are usable to classify whether the detected motion indicates a SAR IN MOTION state that represents user interaction with the communication device.

17. The one or more tangible processor-readable storage media of claim 15, wherein the one or more motion classification conditions are usable to classify whether the detected motion indicates a predefined motion profile representative of a particular pattern of user interaction with the communication device.

18. The one or more tangible processor-readable storage media of claim 17, wherein the operation of adjusting the one or more motion classification parameters comprises adjusting the one or more motion classification parameters based at least in part on the predefined motion profile.

19. The one or more tangible processor-readable storage media of claim 17, wherein the operation of classifying detected motion according to one or more motion classification conditions using one or more motion classification parameters comprises measuring a magnitude of a signal representing frequencies detected in the detected motion that represent human interaction and comparing the magnitude of the signal to a predetermined threshold.

20. The one or more tangible processor-readable storage media of claim 15, wherein the operation of adjusting the one or more motion classification parameters comprises an operation of adjusting one or more of:
   a sample rate at which the detected motion is sampled;
   a decay interval over which a SAR motion state based at least in part on the detected motion is maintained;
   a threshold to which the detected motion is compared;
   a motion profile to which the detected motion is compared; and
   a variable window over which the detected motion is classified in the classifying operation.

* * * * *